US005877305A

United States Patent [19]
Huston et al.

[11] Patent Number: 5,877,305
[45] Date of Patent: Mar. 2, 1999

[54] DNA ENCODING BIOSYNTHETIC BINDING PROTEIN FOR CANCER MARKER

[75] Inventors: James S. Huston, Chester Hill, Mass.; L. L. Houston, Del Mar; David B. Ring, Palo Alto, both of Calif.; Hermann Oppermann, Medway, Mass.

[73] Assignees: Chiron Corporation, Emeryville, Calif.; Creative BioMoelcules, Inc., Hopkinton, Mass.

[21] Appl. No.: 356,786

[22] Filed: Dec. 12, 1994

Related U.S. Application Data

[63] Continuation of Ser. No. 831,967, Feb. 6, 1992, abandoned.
[51] Int. Cl.[6] .................................................. A61K 39/395
[52] U.S. Cl. .................. 536/23.53; 435/69.6; 435/172.3; 435/328; 530/387.3; 424/133.1
[58] Field of Search .............................. 424/180.1, 133.1, 424/135.1, 138.1; 435/69.6, 172.1, 172.3, 240.27, 252.33; 530/387.3; 536/23.53

[56] References Cited

U.S. PATENT DOCUMENTS

| | | |
|---|---|---|
| 4,472,509 | 9/1984 | Gansow et al. .......................... 436/548 |
| 4,479,930 | 10/1984 | Hnatowich ................................ 424/1.1 |
| 4,753,894 | 6/1988 | Frankel et al. ........................... 436/548 |
| 4,946,778 | 8/1990 | Ladner et al. ........................... 435/69.6 |
| 5,091,513 | 2/1992 | Huston et al. ........................... 530/387.3 |
| 5,132,405 | 7/1992 | Huston et al. ........................... 530/387.3 |
| 5,258,498 | 11/1993 | Huston et al. ........................... 530/350 |
| 5,260,203 | 11/1993 | Ladner et al. ........................... 435/172.3 |
| 5,571,894 | 11/1996 | Wels et al. ............................. 530/387.3 |
| 5,587,458 | 12/1996 | King et al. ............................. 530/387.3 |

FOREIGN PATENT DOCUMENTS

| | | |
|---|---|---|
| 0 502 812 A1 | 9/1992 | European Pat. Off. . |
| WO 85/03523 | 8/1985 | WIPO . |
| WO/88/09344 | 1/1988 | WIPO . |
| WO 92/15682 | 9/1992 | WIPO . |

OTHER PUBLICATIONS

Cruise et al Illustrated Dictionary of Immunology CRC Press, New York, p. 280 "specificity", 1995.

New Riverside Unversity Dictionary Houghton Mifflin Company, 'Definition', 1994.

Plückthum (1992) "Mono–and Bivalent Antibody Fragments Produced in *Escherichia coli*: Engineering, Folding and Antigen Binding," *Immunological Reviews*, 130:151–188.

Houston, Abstract from NIH Grant, Ser. No. U01 CA51880–05.

Sefton, B.M. (1988) Trends in Genetics, vol. 4, No. 9, pp. 247–248 "neus about c–erbB2 and HER2".

Bird et al. (1988) Science, vol. 242, pp. 423–426, "Single–Chain Antigen–Binding Proteins".

Shealy, et al. (1990) Abstract Book, Proceedings of the 37th Annual Meeting, No. 290, The Journal of Nuclear Medicine, vol. 31, No. 5, "Characterization and Biodistribution of Tc–99m Labeled Single Chain Antibody Fv Fragment (sFv)".

Colcher, et al. (1990) Journal of the National Cancer Institute, vol. 82 No. 14, pp. 1191–1197, "In Vivo Tumor Targeting of a Recombinant Single–Chain Antigen–Binding Protein".

Whitlow, et al. (1991), Methods: A Comparision to Methods in Enzymology Academic Press, Inc., vol. 2, No. 2, pp. 97–105, "Single–Chain Fv Proteins and Their Fusion Proteins".

Nedelman, et al. (1991) Abstract, The Society of Nuclear Medicine 38th Annual Meeting, No. 32070, "Rapid Infarct Imaging with a New Tc–99m Antimyosin sFv Fragment: Evaluation in Acute Myocardial Infarction in Dogs".

Milenic, et al. (1991) Cancer Research, 51:6363–6371, "Construction, Binding Properties, Metabolism, and Tumor Targeting of a Single–Chain Fv Derived from the Pancarcinoma Monoclonal Antibody CC49".

Wels, et al. (1991) J. Steroid Biochem. Molec. Biol., vol. 43, No. 1–3, pp. 1–7, "Diminution of Antibodies Directed Against Tumor Cell Surface Eipotopes: A Single Chain Fv Fusion Molecular Specifically Recognizes the Extracellular Domain of the c–erbB–2 Receptor".

Aisner et al. (1987) *J. Clin. Oncol.* 5:1523–1533.

Amit et al., (1986) *Science* 233:747–753.

Batra, J.K. et al., (1990) vol. 171, No. 1, pp. 1–6.

Batra, J.K. et al. (1990) *J. Biol. Chem.*, vol. 265, No. 23, pp. 15198–15202.

Bjorn, Michael J., et al. (1985) *Cancer Research*, vol. 45, No. 3, pp. 1214–1221.

McGuire, et al. (Jun. 20, 1990), *J. Nat. Cancer Inst.*, vol. 82, No. 12, pp. 1006–1015.

Satow, et al. (1986), Academic Press Inc., 190:593–604.

Kunkel, Thomas A., *Proc. Natl. Acad. Sci. USA*, vol. 82, pp. 488–492 (1985).

Chen, et al., (Apr. 1985), *DNA*, vol. 4, No. 2, pp. 165–170.

Clackson, T., (Aug. 1991) *Nature*, vol. 352, pp. 624–628.

(List continued on next page.)

*Primary Examiner*—Lila Feisee
*Assistant Examiner*—Julie E. Reeves
*Attorney, Agent, or Firm*—Testa, Hurwitz, Thibeault, LLP

[57] ABSTRACT

Disclosed is DNA encoding a single-chain Fv (sFv) polypeptide defining a binding site which exhibits the immunological binding properties of an immunoglobulin molecule which binds c-erbB-2 or a c-erbB-2-related tumor antigen, the sFv includes at least two polypeptide domains connected by a polypeptide linker spanning the distance between the C-terminus of one domain and the N-terminus of the other, the amino acid sequence of each of the polypeptide domains includes a set of complementarity determining regions (CDRs) interposed between a set of framework regions (FRs), the CDRs conferring immunological binding to the c-erbB-2 or c-erbB-2-related tumor antigen.

3 Claims, 4 Drawing Sheets

OTHER PUBLICATIONS

Colman, et al., (1987) *Nature,* vol. 326, No. 6111, pp. 358–363.

Fisher et al., (1986), *J. of Clin. Onc.,* vol. 4, No. 6, pp. 929–941.

Huston, et al., (1988), *Proc. Natl. Acad. Sci. USA,* vol. 85, pp. 5879–5883.

Huston et al., (1991), *Methods in Enzymology,* 203:46–89.

Orlandi et al., (1989) *Proc. Natl. Acad. Sci., USA,* vol. 86, pp. 3833–3837.

Ring et al., (1991), *Moelcular Immunology,* vol. 28, No. 8, pp. 915–917.

Ring et al., (1989), *Cancer Research,* vol. 49, No. 11, pp. 3070–3080.

Saul et al., (1978)., *The J. of Biol. Chem.,* vol. 253, No. 2., pp.585–595.

Khaw et al., (1980), *Science,* vol. 209, No. 4453, pp. 295–297.

Sheriff et al., (1987), *Proc. Natl. Acad. Sci. USA,* vol. 84, No. 22, pp. 8075–8079.

Stewart, Dr. H.J., (Jul. 25, 1987), *The Lancet,* vol. II, pp. 171–175.

Tai, et al., (1990), *Biochemistry,* vol. 29, No. 35, pp. 8024–8030.

Vogel et al., (1989), *Biochemistry,* vol. 28, No. 7, pp. 2961–2966.

Paul, WE, Fundamental Immunology Raven Press NY 1993 p. 242.

Waldmann, T. A. "Monoclonal Antibodies in Diagnosis and Therapy," *Science* vol. 252:1657–1662, 21 Jun. 1991.

Dillman, R. O., "Monoclonal Antibodies for Treating Cancer," *Annals Int. Med.* 111:592–602, 1 Oct. 1989.

Hird et al., "Immunotherapy with Monoclonal Antibodies," in *Genes and Cancer,* Carney et al., eds., Wiley & Sons, 1990.

Queen et al, "A Humanized Antibody That Binds to the Interleukin–2 Receptor," *Proc. Natl.* Acad. Sci. USA 86:10029–10033, Dec. 1989.

FIG. 1
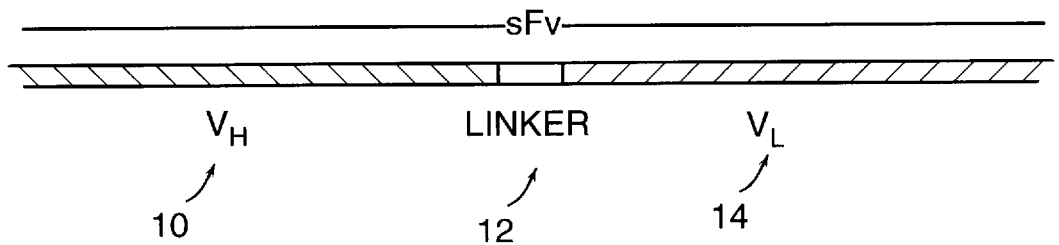
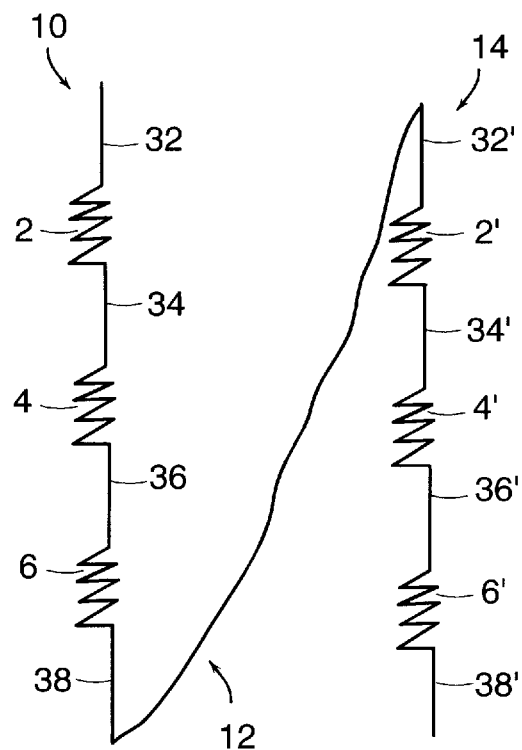
FIG. 2

DNA ENCODING BIOSYNTHETIC BINDING PROTEIN FOR CANCER MARKER

This application is a continuation of application U.S. Ser. No. 07/831,967, filed Feb. 6, 1992, now abandoned.

The work described herein was funded in part by the U.S. Government. Therefore, the U.S. Government has certain rights in the invention.

REFERENCE TO RELATED APPLICATIONS

Related applications include: U.S. Ser. No. 08/133,804, filed Oct. 7, 1993, which is a continuation-in-part of U.S. Ser. No. 07/831,967, filed Feb. 6, 1992, now abandoned; U.S. Ser. Nos. 08/461,838 and 08/461,386, filed Jun. 5, 1995, which are divisionals of U.S. Ser. No. 08/133,804, filed Oct. 7, 1993, which is a continuation-in-part of U.S. Ser. No. 07/831,967, filed Feb. 6, 1992, now abandoned; and U.S. Ser. Nos. 08/462,295 and 08/462,641, filed Jun. 5, 1995, which are continuations of U.S. Ser. No. 08/133,804, filed Oct. 7, 1993, which is a continuation-in-part of U.S. Ser. No. 07/831,967, filed Feb. 6, 1992, now abandoned.

This invention relates in general to novel iosynthetic compositions of matter and, specifically, to biosynthetic antibody binding site (BABS) proteins, and conjugates thereof. Compositions of the invention are useful, for example, in drug and toxin targeting, imaging, immunological treatment of various cancers, and in specific binding assays, affinity purification schemes, and biocatalysis.

BACKGROUND OF THE INVENTION

Carcinoma of the breast is the most common malignancy among women in North America, with 130,000 new cases in 1987. Approximately one in 11 women develop breast cancer in their lifetimes, causing this malignancy to be the second leading cause of cancer death among women in the United States, after lung cancer. Although the majority of women with breast cancer present with completely resectable disease, metastatic disease remains a formidable obstacle to cure. The use of adjuvant chemotherapy or hormonal therapy has definite positive impact on disease-free survival and overall survival in selected subsets of women with completely resected primary breast cancer, but a substantial proportion of women still relapse with metastatic disease (see, e.g., Fisher et al. (1986) J. Clin. Oncol. 4:929–941; "The Scottish trial", Lancet (1987) 2:171–175). In spite of the regularly induced objective responses induced by chemotherapy and hormonal therapy in appropriately selected patients, cure of metastatic breast cancer has not been achieved (see e.g., Aisner, et al. (187) J. Clin. Oncol. 5:1523–1533). To this end, many innovative treatment programs including the use of new agents, combinations of agents, high dose therapy (Henderson, ibid.) and increased dose intensity (Kernan et al. (1988) Clin. Invest. 259:3154–3157) have been assembled. Although improvements have been observed, routine achievement of complete remissions of metastatic disease, the first step toward cure, has not occurred. There remains a pressing need for new approaches to treatment.

The Fv fragment of an immunoglobulin molecule from IgM, and on rare occasions IgG or IgA, is produced by proteolytic cleavage and includes a non-covalent $V_H$–$V_L$ heterodimer representing an intact antigen binding site. A single chain Fv (sFv) polypeptide is a covalently linked $V_H$–$V_L$ heterodimer which is expressed from a gene fusion including $V_H$- and $V_L$-encoding genes connected by a peptide-encoding linker. See Huston et al., 1988, Proc. Nat. Aca. Sci. 85: 5879, hereby incorporated by reference.

U.S. Pat. No. 4,753,894 discloses murine monoclonal antibodies which bind selectively to human breast cancer cells and, when conjugated to ricin A chain, exhibit a TCID 50% against at least one of MCF-7, CAMA-1, SKBR-3, or BT-20 cells of less than about 10 nM. The SKBR-3 cell line is recognized specifically by the monoclonal antibody 520C9. The antibody designated 520C9 is secreted by a murine hybridoma and is now known to recognize c-erbB-2 (Ring et al., 1991, Molecular Immunology 28:915).

SUMMARY OF THE INVENTION

The invention features the synthesis of a class of novel proteins known as single chain Fv (sFv) polypeptides, which include biosynthetic single polypeptide chain binding sites (BABS) and define a binding site which exhibits the immunological binding properties of an immunoglobulin molecule which binds c-erbB-2 or a c-erbB-2-related tumor antigen.

The sFv includes at least two polypeptide domains connected by a polypeptide linker spanning the distance between the carboxy (C)- terminus of one domain and the amino (N)- terminus of the other domain, the amino acid sequence of each of the polypeptide domains including a set of complementarity determining regions (CDRs) interposed between a set of framework regions (FRs), the CDRs conferring immunological binding to c-erbB-2 or a c-erbB-2 related tumor antigen.

In its broadest aspects, this invention features single-chain Fv polypeptides including biosynthetic antibody binding sites, replicable expression vectors prepared by recombinant DNA techniques which include and are capable of expressing DNA sequences encoding these polypeptides, methods for the production of these polypeptides, methods of imaging a tumor expressing c-erbB-2 or a c-erbB-2-related tumor antigen, and methods of treating a tumor using targetable therapeutic agents by virtue of conjugates or fusions with these polypeptides.

As used herein, the term "immunological binding" or "immunologically reactive" refers to the non-covalent interactions of the type that occur between an immunoglobulin molecule and an antigen for which the immunoglobulin is specific; "c-erbB-2" refers to a protein antigen expressed on the surface of tumor cells, such as breast and ovarian tumor cells, which is an approximately 200,000 molecular weight acidic glycoprotein having an isoelectric point of about 5.3 and including the amino acid sequence set forth in SEQ ID NOS:1 and 2. A "c-erbB-2-related tumor antigen" is a protein located on the surface of tumor cells, such as breast and ovarian tumor cells, which is antigenically related to the c-erbB-2 antigen, i.e., bound by an immunoglobulin that is capable of binding the c-erbB-2 antigen, examples of such immunoglobulins being the 520C9, 741F8, and 454C11 antibodies; or which has an amino acid sequence that is at least 80% homologous, preferably 90% homologous, with the amino acid sequence of c-erbB-2. An example of a c-erbB-2 related antigen is the receptor for epidermal growth factor.

An sFv CDR that is "substantially homologous with" an immunoglobulin CDR retains at least 70%, preferably 80% or 90%, of the amino acid sequence of the immunoglobulin CDR, and also retains the immunological binding properties of the immunoglobulin.

The term "domain" refers to that sequence of a polypeptide that folds into a single globular region in its native conformation, and may exhibit discrete binding or functional properties. The term "CDR" or complementarity determining region, as used herein, refers to amino acid sequences which together define the binding affinity and specificity of the natural Fv region of a native immunoglobulin binding site, or a synthetic polypeptide which mimics this function. CDRs typically are not wholly homologous to hypervariable regions of natural Fvs, but rather may also include specific amino acids or amino acid sequences which flank the hypervariable region and have heretofore been considered framework not directly determinative of complementarity. The term "FR" or framework region, as used herein, refers to amino acid sequences which are naturally found between CDRs in immunoglobulins.

Single-chain Fv polypeptides produced in accordance with the invention include biosynthetically-produced novel sequences of amino acids defining polypeptides designed to bind with a preselected c-erbB-2 or related antigen material. The structure of these synthetic polypeptides is unlike that of naturally occurring antibodies, fragments thereof, or known synthetic polypeptides or "chimeric antibodies" in that the regions of the single-chain Fv responsible for specificity and affinity of binding (analogous to native antibody variable ($V_H/V_L$) regions) may themselves be chimeric, e.g., include amino acid sequences derived from or homologous with portions of at least two different antibody molecules from the same or different species. These analogous $V_H$ and $V_L$ regions are connected from the N-terminus of one to the C-terminus of the other by a peptide bonded biosynthetic linker peptide.

The invention thus provides a single-chain Fv polypeptide defining at least one complete binding site capable of binding c-erbB-2 or a c-erbB-2-related tumor antigen. One complete binding site includes a single contiguous chain of amino acids having two polypeptide domains, e.g., $V_H$ and $V_L$, connected by a amino acid linker region. An sFv that includes more than one complete binding site capable of binding a c-erbB-2-related antigen, e.g., two binding sites, will be a single contiguous chain of amino acids having four polypeptide domains, each of which is covalently linked by an amino acid linker region, e.g., $V_{H1}$-linker-$V_{L1}$-linker-$V_{H2}$-linker$V_{L2}$. sFv's of the invention may include any number of complete binding sites ($V_{Hn}$-linker-$V_{Ln}$)$_n$, where n>1, and thus may be a single contiguous chain of amino acids having n antigen binding sites and n×2 polypeptide domains.

In one preferred embodiment of the invention, the single-chain Fv polypeptide includes CDRs that are substantially homologous with at least a portion of the amino acid sequence of CDRs from a variable region of an immunoglobulin molecule from a first species, and includes FRs that are substantially homologous with at least a portion of the amino acid sequence of FRs from a variable region of an immunoglobulin molecule from a second species. Preferably, the first species is mouse and the second species is human.

The amino acid sequence of each of the polypeptide domains includes a set of CDRs interposed between a set of FRs. As used herein, a "set of CDRs" refers to 3 CDRs in each domain, and a "set of FRS" refers to 4 FRs in each domain. Because of structural considerations, an entire set of CDRs from an immunoglobulin may be used, but substitutions of particular residues may be desirable to improve biological activity, e.g., based on observations of conserved residues within the CDRs of immunoglobulin species which bind c-erbB-2 related antigens.

In another preferred aspect of the invention, the CDRs of the polypeptide chain have an amino acid sequence substantially homologous with the CDRs of the variable region of any one of the 520C9, 741F8, and 454C11 monoclonal antibodies. The CDRs of the 520C9 antibody are set forth in the Sequence Listing as amino acid residue numbers 31 through 35, 50 through 66, 99 through 104, 157 through 167, 183 through 189, and 222 though 230 of Seq. ID Nos. 3 and 4.

In one embodiment, the sFv is a humanized hybrid molecule which includes CDRs from the mouse 520C9 antibody interposed between FRs derived from one or more human immunoglobulin molecules. This hybrid sFv thus contains binding regions which are highly specific for the c-erbB-2 antigen or c-erbB-2-related antigens held in proper immunochemical binding conformation by human FR amino acid sequences, and thus will be less likely to be recognized as foreign by the human body.

In another embodiment, the polypeptide linker region includes the amino acid sequence set forth in the Sequence Listing as amino acid residue numbers 123 through 137 in SEQ ID NOS:3 and 4, and as amino acid residues 1–16 in SEQ ID NOS:11 and 12. In other embodiments, the linker sequence has the amino acid sequence set forth in the Sequence Listing as amino acid residues 410–424 in SEQ ID NOS:4 and 10, or the amino acid sequence of residues 1–15 in SEQ ID NOS:13 and 14.

The single polypeptide chain described above also may include a remotely detectable moiety bound thereto to permit imaging or radioimmunotherapy of tumors bearing a c-erbB-2 or related tumor antigen. "Remotely detectable" moiety means that the moiety that is bound to the sFv may be detected by means external to and at a distance from the site of the moiety. Preferable remotely detectable moieties for imaging include radioactive atom such as $^{99m}$Technetium ($^{99m}$Tc), a gamma emitter. Preferable nucleotides for high dose radioimmunotherapy include radioactive atoms such as, ($^{90}$Yttrium ($^{90}$Yt), $^{131}$Iodine ($^{131}$I) or $^{111}$Indium ($^{111}$In).

In addition, the sFv may include a fusion protein derived from a gene fusion, such that the expressed sFv fusion protein includes an ancillary polypeptide that is peptide bonded to the binding site polypeptide. In some preferred aspects, the ancillary polypeptide segment also has a binding affinity for a c-erbB-2 or related antigen and may include a third and even a fourth polypeptide domain, each comprising an amino acid sequence defining CDRs interposed between FRs, and which together form a second single polypeptide chain biosynthetic binding site similar to the first described above.

In other aspects, the ancillary polypeptide sequence forms a toxin linked to the N or C terminus of the sFv, e.g., at least a toxic portion of Pseudomonas exotoxin, phytolaccin, ricin, ricin A chain, or diphtheria toxin, or other related proteins known as ricin A chain-like ribosomal inhibiting proteins, i.e., proteins capable of inhibiting protein synthesis at the level of the ribosome, such as pokeweed antiviral protein, gelonin, and barley ribosomal protein inhibitor. In still another aspect, the sFv may include at least a second ancillary polypeptide or moiety which will promote internalization of the sFv.

The invention also includes a method for producing sFv, which includes the steps of providing a replicable expression vector which includes and which expresses a DNA sequence encoding the single polypeptide chain; transfecting the expression vector into a host cell to produce a transformant; and culturing the transformant to produce the sFv polypeptide.

The invention also includes a method of imaging a tumor expressing a c-erbB-2 or related tumor antigen. This method includes the steps of providing an imaging agent including a single-chain Fv polypeptide as described above, and a remotely detectable moiety linked thereto; administering the imaging agent to an organism harboring the tumor in an amount of the imaging agent with a physiologically-compatible carrier sufficient to permit extracorporeal detection of the tumor; and detecting the location of the moiety in the subject after allowing the agent to bind to the tumor and unbound agent to have cleared sufficiently to permit visualization of the tumor image.

The invention also includes a method of treating cancer by inhibiting in vivo growth of a tumor expressing a c-erbB-2 or related antigen, the method including administering to a cancer patient a tumor inhibiting amount of a therapeutic agent which includes an sFv of the invention and at least a first moiety peptide bonded thereto, and which has the ability to limit the proliferation of a tumor cell.

Preferably, the first moiety includes a toxin or a toxic fragment thereof, e.g., ricin A; or includes a radioisotope sufficiently radioactive to inhibit proliferation of the tumor cell, e.g., $^{90}$Yt, $^{111}$In, or $^{131}$I. The therapeutic agent may further include at least a second moiety that improves its effectiveness.

The clinical administration of the single-chain Fv or appropriate sFv fusion proteins of the invention, which display the activity of native, relatively small Fv of the corresponding immunoglobulin, affords a number of advantages over the use of larger fragments or entire antibody molecules. The single chain Fv and sFv fusion proteins of this invention offer fewer cleavage sites to circulating proteolytic enzymes and thus offer greater stability. They reach their target tissue more rapidly, and are cleared more quickly from the body, which makes them ideal imaging agents for tumor detection and ideal radioimmunotherapeutic agents for tumor killing. They also have reduced non-specific binding and immunogenicity relative to murine immunoglobulins. In addition, their expression from single genes facilitates targeting applications by fusion to other toxin proteins or peptide sequences that allow specific coupling to other molecules or drugs. In addition, some sFv analogues or fusion proteins of the invention have the ability to promote the internalization of c-erbB-2 or related antigens expressed on the surface of tumor cells when they are bound together at the cell surface. These methods permit the selective killing of cells expressing such antigens with the single-chain-Fv-toxin fusion of appropriate design. sFv-toxin fusion proteins of the invention possess 15–200-fold greater tumor cell killing activity than conjugates which include a toxin that is chemically crosslinked to whole antibody or Fab.

Overexpression of c-erbB-2 or related receptors on malignant cells thus allows targeting of sFv species to the tumor cells, whether the tumor is well-localized or metastatic. In the above cases, the internalization of sFv-toxin fusion proteins permits specific destruction of tumor cells bearing the over expressed c-erbB-2 or related antigen. In other cases, depending on the infected cells, the nature of the malignancy, or other factors operating in a given individual, the same c-erbB-2 or related receptors may be poorly internalized or even represent a static tumor antigen population. In this event, the single-chain Fv and its fusion proteins can also be used productively, but in a different mode than applicable to internalization of the toxin fusion. Where c-erbB-2 receptor/sFv or sFv fusion protein complexes are poorly internalized, toxins, such as ricin A chain, which operate cytoplasmically by inactivation of ribosomes, are not effective to kill cells. Nevertheless, single-chain unfused Fv is useful, e.g., for imaging or radioimmunotherapy, and bispecific single-chain Fv fusion proteins of various designs, i.e., that have two distinct binding sites on the same polypeptide chain, can be used to target via the two antigens for which the molecule is specific. For example, a bispecific single-chain antibody may have specificity for both the c-erbB-2 and CD3 antigens, the latter of which is present on cytotoxic lymphocytes (CTLs). This bispecific molecule could thus mediate antibody dependent cellular cytotoxicity (ADCC) that results in CTL-induced lysis of tumor cells. Similar results could be obtained using a bispecific single-chain Fv specific for c-erbB-2 and the Fc$_\gamma$ receptor type I or II. Other bispecific sFv formulations include domains with c-erbB-2 specificity paired with a growth factor domain specific for hormone or growth factor receptors, such as receptors for transferrin or epidermal growth factor (EGF).

BRIEF DESCRIPTION OF THE DRAWINGS

The foregoing and other objects of this invention, the various features thereof, as well as the invention itself, may be more fully understood from the following description, when read together with the accompanying drawings in the following figures.

FIG. 1 is a schematic drawing of a DNA construct encoding an sFv of the invention, which shows the $V_H$ and $V_L$ encoding domains and the linker region; FIG. 2 is a schematic drawing of the structure of Fv illustrating $V_H$ and $V_L$ domains, each of which comprises three complementarity determining regions (CDRs) and four framework regions (FRs) for monoclonal 520C9, a well known and characterized murine monoclonal antibody specific for c-erbB-2;

FIG. 3 is an sFv having a pendant leader sequence, FIG. 4 is an sfv-toxin (or other ancillary protein) construct, and FIG. 5 is a bivalent or bispecific sFv construct; FIG. 6 is a bivalent sFv having a pendant protein attached to the carboxyl-terminal end; FIG. 7 is a bivalent sFv having pendant proteins attached to both amino- and carboxyl-terminal ends.

DETAILED DESCRIPTION OF THE INVENTION

Figure 3:
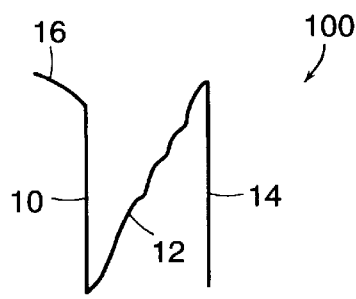
FIGS. 3–7 are schematic representations of embodiments of the invention, each of which comprises a biosynthetic single-chain Fv polypeptide which recognizes a c-erbB-2-related antigen.
Figure 4:
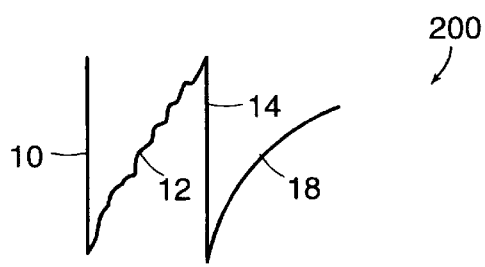
Figure 5:
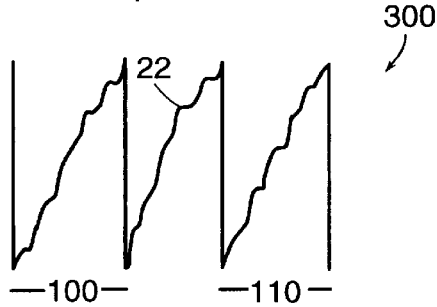

Disclosed are single-chain Fv's and sFv fusion proteins having affinity for a c-erbB-2-related antigen expressed at high levels on breast and ovarian cancer cells and on other tumor cells as well, in certain other forms of cancer. The polypeptides are characterized by one or more sequences of amino acids constituting a region which behaves as a biosynthetic antibody binding site. As shown in FIG. 1, the sites comprise heavy chain variable region ($V_H$) 10, light chain variable region ($V_L$) 14 single chains wherein $V_H$ 10 and $V_L$ 14 are attached by polypeptide linker 12. The binding domains include CDRs 2, 4, 6 and 2', 4', 6' from immunoglobulin molecules able to bind a c-erbB-2-related tumor antigen linked to FRs 32, 34, 36, 38 and 32', 34', 36' 38' which may be derived from a separate immunoglobulin. As shown in FIGS. 3, 4, and 5, the BABS single polypeptide chains ($V_H$ 10, $V_L$ 14 and linker 12) may also include remotely detectable moieties and/or other polypeptide sequences 16, 18, or 22, which function e.g., as an enzyme, toxin, binding site, or site of attachment to an immobilization matrix or radioactive atom. Also disclosed are methods for producing the proteins and methods of their use.

The single-chain Fv polypeptides of the invention are biosynthetic in the sense that they are synthesized and recloned in a cellular host made to express a protein encoded by a plasmid which includes genetic sequence based in part on synthetic DNA, that is, a recombinant DNA made from ligation of plural, chemically synthesized and recloned oligonucleotides, or by ligation of fragments of DNA derived from the genome of a hybridoma, mature B cell clone, or a cDNA library derived from such natural sources. The proteins of the invention are properly characterized as "antibody binding sites" in that these synthetic single polypeptide chains are able to refold into a 3-dimensional conformation designed specifically to have affinity for a preselected c-erbB-2 or related tumor antigen. Single-chain Fv's may be produced as described in U.S. Ser. No. 07/955,399, filed Oct. 1, 1992, now U.S. Pat. No. 5,258,498, the disclosure of which is incorporated herein by reference. U.S. Ser. No. 07/955,399 is a continuation of U.S. Ser. No. 07/342,449, filed Jan. 23, 1989, now abandoned, which is a continuation-in-part of U.S. Ser. No. 07/052,880, filed May 21, 1987, now abandoned. The polypeptides of the invention are antibody-like in that their structure is patterned after regions of native antibodies known to be responsible for c-erbB-2-related antigen recognition.

More specifically, the structure of these biosynthetic antibody binding sites (BABS) in the region which imparts the binding properties to the protein, is analogous to the Fv region of a natural antibody to a c-erbB-2 or related antigen. It includes a series of regions consisting of amino acids defining at least three polypeptide segments which together form the tertiary molecular structure responsible for affinity and binding. The CDRs are held in appropriate conformation by polypeptide segments analogous to the framework regions of the Fv fragment of natural antibodies.

The CDR and FR polypeptide segments are designed empirically based on sequence analysis of the Fv region of preexisting antibodies, such as those described in U.S. Pat. No. 4,753,894, herein incorporated by reference, or of the DNA encoding such antibody molecules.

One such antibody, 520C9, is a murine monoclonal antibody that is known to react with an antigen expressed by the human breast cancer cell line SK-Br-3 (U.S. Pat. No. 4,753, 894). The antigen is an approximately 200 kD acidic glycoprotein that has an isoelectric point of 5.3, and is present at about 5 million copies per cell. The association constant measured using radiolabelled antibody is approximately $4.6 \times 10^8$ $M^{-1}$.

In one embodiment, the amino acid sequences constituting the FRs of the single polypeptide chains are analogous to the FR sequences of a first preexisting antibody, for example, a human IgG. The amino acid sequences constituting the CDRs are analogous to the sequences from a second, different preexisting antibody, for example, the CDRs of a rodent or human IgG which recognizes c-erbB-2 or related antigens expressed on the surface of ovarian and breast tumor cells. Alternatively, the CDRs and FRs may be copied in their entirety from a single preexisting antibody from a cell line which may be unstable or, difficult to culture; e.g., an sFv-producing cell line that is based upon a murine, mouse/human, or human monoclonal antibody-secreting cell line.

Practice of the invention enables the design and biosynthesis of various reagents, all of which are characterized by a region having affinity for a preselected c-erbB-2 or related antigen. Other regions of the biosynthetic protein are designed with the particular planned utility of the protein in mind. Thus, if the reagent is designed for intravascular use in mammals, the FRs may include amino acid sequences that are similar or identical to at least a portion of the FR amino acids of antibodies native to that mammalian species. On the other hand, the amino acid sequences that include the CDRs may be analogous to a portion of the amino acid sequences from the hypervariable region (and certain flanking amino acids) of an antibody having a known affinity and specificity for a c-erbB-2 or related antigen that is from, e.g., a mouse or rat, or a specific human antibody or immunoglobulin.

Other sections of native immunoglobulin protein structure, e.g., $C_H$ and $C_L$, need not be present and normally are intentionally omitted from the biosynthetic proteins of this invention. However, the single polypeptide chains of the invention may include additional polypeptide regions defining a leader sequence or a second polypeptide chain that is bioactive, e.g., a cytokine, toxin, ligand, hormone, immunoglobulin domain(s), or enzyme, or a site onto which a toxin, drug, or a remotely detectable moiety, e.g., a radionuclide, can be attached.

One useful toxin is ricin, an enzyme from the castor bean that is highly toxic, or the portion of ricin that confers toxicity. At concentrations as low as 1 ng/ml ricin efficiently inhibits the growth of cells in culture. The ricin A chain has a molecular weight of about 30,000 and is glycosylated. The ricin B chain has a larger size (about 34,000 molecular weight) and is also glycosylated. The B chain contains two galactose binding sites, one in each of the two domains in the folded subunit. The crystallographic structure for ricin shows the backbone tracing of the A chain. There is a cleft, which is probably the active site, that runs diagonally across the molecule. Also present is a mixture of α-helix, β-structure, and irregular structure in the molecule.

The A chain enzymatically inactivates the 60S ribosomal subunit of eucaryotic ribosomes. The B chain binds to galactose-based carbohydrate residues on the surfaces of cells. It appears to be necessary to bind the toxin to the cell surface, and also facilitates and participates in the mechanics of entry of the toxin into the cell. Because all cells have galactose-containing cell surface receptors, ricin inhibits all types of mammalian cells with nearly the same efficiency.

Ricin A chain and ricin B chain are encoded by a gene that specifies both the A and B chains. The polypeptide synthesized from the mRNA transcribed from the gene contains A chain sequences linked to B chain sequences by a 'J' (for joining) peptide. The J peptide fragment is removed by post-translational modification to release the A and B chains. However, A and B chains are still held together by the interchain disulfide bond. The preferred form of ricin is recombinant A chain as it is totally free of B chain and, when expressed in *E. coli*, is unglycosylated and thus cleared from the blood more slowly than the gycosylated form. The specific activity of the recombinant ricin A chain against ribosomes and that of native A chain isolated from castor bean ricin are equivalent. An amino acid sequence and corresponding nucleic acid sequence of ricin A chain is set forth in the Sequence Listing as SEQ ID NOS:7 and 8.

Recombinant ricin A chain, plant-derived ricin A chain, deglycosylated ricin A chain, or derivatives thereof, can be targeted to a cell expressing a c-erbB-2 or related antigen by the single-chain Fv polypeptide of the present invention. To do this, the sFv may be chemically crosslinked to the ricin A chain form of choice, or in a preferred embodiment a single-chain Fv-ricin A chain immunotoxin may be formed by fusing the single-chain Fv polypeptide to one or more ricin A chains through the corresponding gene fusion. By replacing the B chain of ricin with an antibody binding site to c-erbB-2 or related antigens, the A chain is guided to such antigens on the cell surface. In this way the selective killing of tumor cells expressing these antigens can be achieved. This selectivity has been demonstrated in many cases against cells grown in culture. It depends on the presence or absence of antigens on the surface of the cells to which the immunotoxin is directed.

The invention includes the use of humanized single-chain-Fv binding sites as part of imaging methods and tumor therapies. The proteins may be administered by intravenous or intramuscular injection. Effective dosages for the single-chain Fv constructs in antitumor therapies or in effective tumor imaging can be determined by routine experimentation, keeping in mind the objective of the treatment.

The pharmaceutical forms suitable for injectable use include sterile aqueous solutions or dispersions. In all cases, the form must be sterile and must be fluid so as to be easily administered by syringe. It must be stable under the conditions of manufacture and storage, and must be preserved against the contaminating action of microorganisms. This may, for example, be achieved by filtration through a sterile 0.22 micron filter and/or lyophilization followed by sterilization with a gamma ray source.

Sterile injectable solutions are prepared by incorporating the single chain constructs of the invention in the required amount in the appropriate solvent, such as sodium phosphate-buffered saline, followed by filter sterilization. As used herein, "a physiologically acceptable carrier" includes any and all solvents, dispersion media, antibacterial and antifungal agents that are non-toxic to humans, and the like. The use of such media and agents for pharmaceutically active substances is well known in the art. The media or agent must be compatible with maintenance of proper conformation of the single polypeptide chains, and its use in the therapeutic compositions. Supplementary active ingredients can also be incorporated into the compositions.

A bispecific single-chain Fv could also be fused to a toxin. For example, a bispecific sFv construct with specificity for c-erbB-2 and the transferrin receptor, a target that is rapidly internalized, would be an effective cytolytic agent due to internalization of the transferrin receptor/sFv-toxin complex. An sFv fusion protein may also include multiple protein domains on the same polypeptide chain, e.g., EGF-sFv-ricin A, where the EGF domain promotes internalization of toxin upon binding of sFv through interaction with the EGF receptor.

The single polypeptide chains of the invention can be labelled with radioisotopes such as Iodine-131, Indium-111, and Technetium-99m, for example. Beta emitters such as Technetium-99m and Indium-111 are preferred because they are detectable with a gamma camera and have favorable half-lives for imaging in vivo. The single polypeptide chains can be labelled, for example, with radioactive atoms and as Yttrium-90, Technetium-99m, or Indium-111 via a conjugated metal chelator (see, e.g., Khaw et al. (1980) Science 209:295; Gansow et al., U.S. Pat. No. 4,472,509; Hnatowich, U.S. Pat. No. 4,479,930), or by other standard means of isotope linkage to proteins known to those with skill in the art.

The invention thus provides intact binding sites for c-erbB-2 or related antigens that are analogous to $V_H$-$V_L$ dimers linked by a polypeptide sequence to form a composite $(V_H\text{-linker-}V_L)_n$ or $(V_L\text{-linker-}V_H)_n$ polypeptide, where n is equal to or greater than 1, which is essentially free of the remainder of the antibody molecule, and which may include a detectable moiety or a third polypeptide sequence linked to each $V_H$ or $V_L$.

FIGS. 3–7 illustrate examples of protein structures embodying the invention that can be produced by following the teaching disclosed herein. All are characterized by at least one biosynthetic sFv single chain segment defining a binding site, and containing amino acid sequences including CDRs and FRs, often derived from different immunoglobulins, or sequences homologous to a portion of CDRs and FRs from different immunoglobulins.

FIG. 3 depicts single polypeptide chain sFv 100 comprising polypeptide 10 having an amino acid sequence analogous to the heavy chain variable region ($V_H$) of a given anti-c-erbB-2 monoclonal antibody, bound through its carboxyl end to polypeptide linker 12, which in turn is bound to polypeptide 14 having an amino acid sequence analogous to the light chain variable region ($V_L$) of the anti-c-erbB-2 monoclonal. Of course, the light and heavy chain domains may be in reverse order. Linker 12 should be at least long enough (e.g., about 10 to 15 amino acids or about 40 Angstroms) to permit chains 10 and 14 to assume their proper conformation and interdomain relationship.

Linker 12 may include an amino acid sequence homologous to a sequence identified as "self" by the species into which it will be introduced, if drug use is intended. Unstructured, hydrophilic amino acid sequences are preferred. Such linker sequences are set forth in the Sequence Listing as amino acid residue numbers 116 through 135 in SEQ ID Nos. 3 and 4, and may include part of the 15 amino acid linker sequences set forth in the Sequence Listing as SEQ ID Nos.:12 and 14.

Other proteins or polypeptides may be attached to either the amino or carboxyl terminus of protein of the type illustrated in FIG. 3. As an example, leader sequence 16 is shown extending from the amino terminal end of $V_H$ domain 10.

FIG. 4 depicts another type of reagent 200 including a single polypeptide chain 100 and a pendant protein 18. Attached to the carboxyl end of the polypeptide chain 100 (which includes the FR and CDR sequences constituting an immunoglobulin binding site) is a pendant protein 18 consisting of, for example, a toxin or toxic fragment thereof, binding protein, enzyme or active enzyme fragment, or site of attachment for an imaging agent (e.g., to chelate a radioactive ion such as Indium-111).

FIG. 5 illustrates single chain polypeptide 300 including second single chain polypeptide 110 of the invention having the same or different specificity and connected via peptide linker 22 to the first single polypeptide chain 100.

Figure 6:
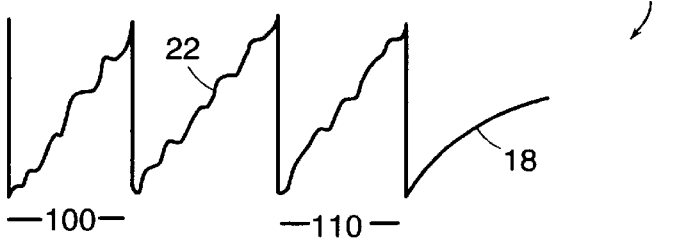

FIG. 6 illustrates single chain polypeptide 400 which includes single polypeptide chains 110 and 100 linked together by linker 22, and pendant protein 18 attached to the carboxyl end of chain 110.

Figure 7:
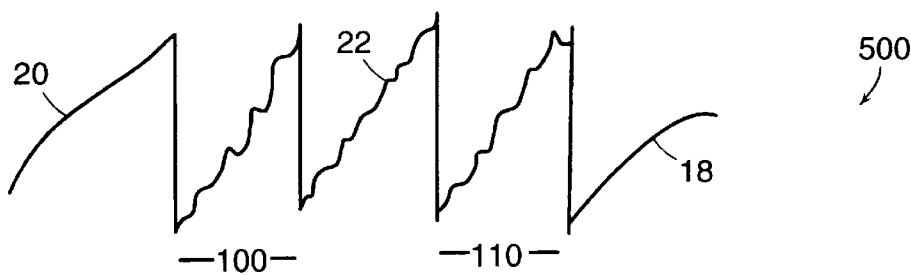

FIG. 7 illustrates single polypeptide chain 500 which includes chain 400 of FIG. 6 and pendant protein 20 (EGF) attached to the amino terminus of chain 400.

As is evident from FIGS. 3–7, single chain proteins of the invention may resemble beads on a string by including multiple biosynthetic binding sites, each binding site having unique specificity, or repeated sites of the same specificity to increase the avidity of the protein. As is evidenced from the foregoing, the invention provides a large family of reagents comprising proteins, at least a portion of which defines a binding site patterned after the variable region or regions of immunoglobulins to c-erbB-2 or related antigens.

The single chain polypeptides of the invention are designed at the DNA level. The synthetic DNAs are then expressed in a suitable host system, and the expressed proteins are collected and renatured if necessary.

The ability to design the single polypeptide chains of the invention depends on the ability to identify monoclonal antibodies of interest, and then to determine the sequence of the amino acids in the variable region of these antibodies, or the DNA sequence encoding them. Hybridoma technology enables production of cell lines secreting antibody to essentially any desired substance that elicits an immune response. For example, U.S. Pat. No. 4,753,894 describes some monoclonal antibodies of interest which recognize c-erbB-2 related antigens on breast cancer cells, and explains how such antibodies were obtained. One monoclonal antibody that is particularly useful for this purpose is 520C9 (Bjorn et al. (1985) Cancer Res. 45:124–1221; U.S. Pat. No. 4,753, 894). This antibody specifically recognizes the c-erbB-2 antigen expressed on the surface of various tumor cell lines, and exhibits very little binding to normal tissues. Alternative sources of sFv sequences with the desired specificity can take advantage of phage antibody and combinatorial library methodology. Such sequences would be based on cDNA from mice which were preimmunized with tumor cell membranes or c-erb-B-2 or c-erbB-2-related antigenic fragments or peptides. (See, e.g., Clackson et al, Nature 352 624–628 (1991))

The process of designing DNA that encodes the single polypeptide chain of interest can be accomplished as follows. RNA encoding the light and heavy chains of the desired immunoglobulin can be obtained from the cytoplasm of the hyridoma producing the immunoglobulin. The mRNA can be used to prepare the cDNA for subsequent isolation of $V_H$ and $V_L$ genes by PCR methodology known in the art (Sambrook et al., eds., Molecular Cloning, 1989, Cold Spring Harbor Laboratories Press, NY). The N-terminal amino acid sequence of H and L chain may be independently determined by automated Edman sequencing; if necessary, further stretches of the CDRs and flanking FRs can be determined by amino acid sequencing of the H and L chain V region fragments. Such sequence analysis is now conducted routinely. This knowledge permits one to design synthetic primers for isolation of $V_H$ and $V_L$ genes from hybridoma cells that make monoclonal antibodies known to bind the c-erbB-2 or related antigen. These V genes will encode the Fv region that binds c-erbB-2 in the parent antibody.

Still another approach involves the design and construction of synthetic V genes that will encode an Fv binding site specific for c-erbB-2 or related receptors. For example, with the help of a computer program such as, for example, Compugene, and known variable region DNA sequences, one may design and directly synthesize native or near-native FR sequences from a first antibody molecule, and CDR sequences from a second antibody molecule. The $V_H$ and $V_L$ sequences described above are linked together directly via an amino acid chain or linker connecting the C-terminus of one chain with the N-terminus of the other.

These genes, once synthesized, may be cloned with or without additional DNA sequences coding for, e.g., a leader peptide which facilitates secretion or intracellular stability of a fusion polypeptide, or a leader or trailing sequence coding for a second polypeptide. The genes then can be expressed directly in an appropriate host cell.

By directly sequencing an antibody to a c-erbB-2 or related antigen, or obtaining the sequence from the literature, in view of this disclosure, one skilled in the art can produce a single chain Fv comprising any desired CDR and FR. For example, using the DNA sequence for the 520C9 monoclonal antibody set forth in the Sequence Listing as SEQ ID NO:3, a single chain polypeptide can be produced having a binding affinity for a c-erbB-2 related antigen. Expressed sequences may be tested for binding and empirically refined by exchanging selected amino acids in relatively conserved regions, based on observation of trends in amino acid sequence data and/or computer modeling techniques. Significant flexibility in $V_H$ and $V_L$ design is possible because alterations in amino acid sequences may be made at the DNA level.

Accordingly, the construction of DNAs encoding the single-chain Fv and sFv fusion proteins of the invention can be done using known techniques involving the use of various restriction enzymes which make sequence-specific cuts in DNA to produce blunt ends or cohesive ends, DNA ligases, techniques enabling enzymatic addition of sticky ends to blunt-ended DNA, construction of synthetic DNAs by assembly of short or medium length oligonucleotides, cDNA synthesis techniques, and synthetic probes for isolating immunoglobulin genes. Various promoter sequences and other regulatory RNA sequences used in achieving expression, and various type of host cells are also known and available. Conventional transfection techniques, and equally conventional techniques for cloning and subcloning DNA are useful in the practice of this invention and known to those skilled in the art. Various types of vectors may be used such as plasmids and viruses including animal viruses and bacteriophages. The vectors may exploit various marker genes which impart to a successfully transfected cell a detectable phenotypic property that can be used to identify which of a family of clones has successfully incorporated the recombinant DNA of the vector.

Of course, the processes for manipulating, amplifying, and recombining DNA which encode amino acid sequences of interest are generally well known in the art, and therefore, not described in detail herein. Methods of identifying the isolated V genes encoding antibody Fv regions of interest are well understood, and described in the patent and other literature. In general, the methods involve selecting genetic material coding for amino acid sequences which define the CDRs and FRs of interest upon reverse transcription, according to the genetic code.

One method of obtaining DNA encoding the single-chain Fv disclosed herein is by assembly of synthetic oligonucleotides produced in a conventional, automated, polynucleotide synthesizer followed by ligation with appropriate ligases. For example, overlapping, complementary DNA fragments comprising 15 bases may be synthesized semi-manually using phosphoramidite chemistry, with end segments left unphosphorylated to prevent polymerization during ligation. One end of the synthetic DNA is left with a "sticky end" corresponding to the site of action of a particular restriction endonuclease, and the other end is left with an end corresponding to the site of action of another restriction endonuclease. Alternatively, this approach can be fully automated. The DNA encoding the single chain polypeptides may be created by synthesizing longer single strand fragments (e.g., 50–100 nucleotides long) in, for example, a Biosearch oligonucleotide synthesizer, and then ligating the fragments.

Additional nucleotide sequences encoding, for example, constant region amino acids or a bioactive molecule may also be linked to the gene sequences to produce a bifunctional protein.

For example, the synthetic genes and DNA fragments designed as described above may be produced by assembly of chemically synthesized oligonucleotides. 15–100 mer oligonucleotides may be synthesized on a Biosearch DNA Model 8600 Synthesizer, and purified by polyacrylamide gel electrophoresis (PAGE) in Tris-Borate-EDTA buffer (TBE). The DNA is then electroeluted from the gel. Overlapping oligomers may be phosphorylated by T4 polynucleotide kinase and ligated into larger blocks which may also be purified by PAGE.

The blocks or the pairs of longer oligonucleotides may be cloned in E. coli using a suitable cloning vector, e.g., pUC. Initially, this vector may be altered by single-strand mutagenesis to eliminate residual six base altered sites. For example, $V_H$ may be synthesized and cloned into pUC as five primary blocks spanning the following restriction sites: (1) EcoRI to first NarI site; (2) first NarI to XbaI; (3) XbaI to SalI; (4) SalI to NcoI; and (5) NcoI to BamHI. These cloned fragments may then be isolated and assembled in several three-fragment ligations and cloning steps into the pUC8 plasmid. Desired ligations, selected by PAGE, are then transformed into, for example, E. coli strain JM83, and plated onto LB Ampicillin+Xgal plates according to standard procedures. The gene sequence may be confirmed by supercoil sequencing after cloning, or after subcloning into M13 via the dideoxy method of Sanger (Molecular Cloning, 1989, Sambrook et al., eds, 2d ed., Vol. 2, Cold Spring Harbor Laboratory Press, NY).

The engineered genes can be expressed in appropriate prokaryotic hosts such as various strains of E. coli, and in eucaryotic hosts such as Chinese hamster ovary cells (CHO), mouse myeloma, hybridoma, transfectoma, and human myeloma cells.

If the gene is to be expressed in E. coli, it may first be cloned into an expression vector. This is accomplished by positioning the engineered gene downstream from a promoter sequence such as Trp or Tac, and a gene coding for a leader polypeptide such as fragment B (FB) of staphylococcal protein A. The resulting expressed fusion protein accumulates in refractile bodies in the cytoplasm of the cells, and may be harvested after disruption of the cells by French press or sonication. The refractile bodies are solubilized, and the expressed fusion proteins are cleaved and refolded by the methods already established for many other recombinant proteins (Huston et al, 1988, supra) or, for direct expression methods, there is no leader and the inclusion bodies may be refolded without cleavage (Huston et al, 1991, Methods in Enzymology, vol 203, pp 46–88).

For example, subsequent proteolytic cleavage of the isolated sFv from their leader sequence fusions can be performed to yield free sFvs, which can be renatured to obtain an intact biosynthetic, hybrid antibody binding site. The cleavage site preferably is immediately adjacent the sFv polypeptide and includes one amino acid or a sequence of amino acids exclusive of any one amino acid or amino acid sequence found in the amino acid structure of the single polypeptide chain.

The cleavage site preferably is designed for specific cleavage by a selected agent. Endopeptidases are preferred, although non-enzymatic (chemical) cleavage agents may be used. Many useful cleavage agents, for instance, cyanogen bromide, dilute acid, trypsin, Staphylococcus aureus V-8 protease, post-proline cleaving enzyme, blood coagulation Factor Xa, enterokinase, and renin, recognize and preferentially or exclusively cleave at particular cleavage sites. One currently preferred peptide sequence cleavage agent is V-8 protease. The currently preferred cleavage site is at a Glu residue. Other useful enzymes recognize multiple residues as a cleavage site, e.g., factor Xa or enterokinase. Dilute acid preferentially leaves the peptide bond between Asp-Pro residues, and CNBr in acid cleaves after Met, unless it is followed by Tyr.

If the engineered gene is to be expressed in eucaryotic hybridoma cells, the conventional expression system for immunoglobulins, it is first inserted into an expression vector containing, for example, the immunoglobulin promoter, a secretion signal, immunoglobulin enhancers, and various introns. This plasmid may also contain sequences encoding another polypeptide such as all or part of a constant region, enabling an entire part of a heavy or light chain to be expressed, or at least part of a toxin, enzyme, cytokine, or hormone. The gene is transfected into myeloma cells via established electroporation or protoplast fusion methods. Cells so transfected may then express $V_H$-linker-$V_L$ or $V_L$-linker-$V_H$ single-chain Fv polypeptides, each of which may be attached in the various ways discussed above to a protein domain having another function (e.g., cytotoxicity).

For construction of a single contiguous chain of amino acids specifying multiple binding sites, restriction sites at the boundaries of DNA encoding a single binding site (i.e., $V_H$-linker-$V_L$) are utilized or created, if not already present. DNAs encoding single binding sites are ligated and cloned into shuttle plasmids, from which they may be further assembled and cloned into the expression plasmid. The order of domains will be varied and spacers between the domains provide flexibility needed for independent folding of the domains. The optimal architecture with respect to expression levels, refolding and functional activity will be determined empirically. To create bivalent sFv's, for example, the stop codon in the gene encoding the first binding site is changed to an open reading frame, and several glycine plus serine codons including a restriction site such as BamHI (encoding Gly-Ser) or XhoI (encoding Gly-Ser-Ser) are put in place. The second sFv gene is modified similarly at its 5' end, receiving the same restriction site in the same reading frame. The genes are combined at this site to produce the bivalent sFv gene.

Linkers connecting the C-terminus of one domain to the N-terminus of the next generally comprise hydrophilic amino acids which assume an unstructured configuration in physiological solutions and preferably are free of residues having large side groups which might interfere with proper folding of the $V_H$, $V_L$, or pendant chains. One useful linker has the amino acid sequence $[(Gly)_4 Ser]_3$ (see SEQ ID NOS:9 and 10, residue numbers 410–421). One currently preferred linker has the amino acid sequence comprising 2 or 3 repeats of $[(Ser)_4 Gly]_2$ such as $[(Ser)_4 Gly]_3$ (see SEQ ID NOS:3 and 4).

The invention is illustrated further by the following non-limiting Examples.

EXAMPLES

1. Antibodies to c-erbB-2 Related Antigens

Monoclonal antibodies against breast cancer have been developed using human breast cancer cells or membrane extracts of the cells for immunizing mice, as described in Frankel et al. (1985) J. Biol. Resp. Modif. 4:273–286, hereby incorporated by reference. Hybridomas have been made and selected for production of antibodies using a panel of normal and breast cancer cells. A panel of eight normal tissue membranes, a fibroblast cell line, and frozen sections of breast cancer tissues were used in the screening. Candidates that passed the first screening were further tested on 16 normal tissue sections, 5 normal blood cell types, 11 non-breast neoplasm sections, 21 breast cancer sections, and 14 breast cancer cell lines. From this selection, 127 antibodies were selected. Irrelevant antibodies and nonbreast cancer cell lines were used in control experiments.

Useful monoclonal antibodies were found to include 520C9, 454C11 (A.T.C.C. Nos. HB8696 and HB8484, respectively) and 741F8. Antibodies identified as selective for breast cancer in this screen reacted against five different antigens. The sizes of the antigens that the antibodies recognize: 200 kD; a series of proteins that are probably degradation products with Mr's of 200 kD, 93 kD, 60 kD, and 37 kD; 180 kD (transferrin receptor); 42 kD; and 55 kD, respectively. Of the antibodies directed against the five classes of antigens, the most specific are the ones directed against the 200 kD antigen, 520C9 being a representative antibody for that antigen class. 520C9 reacts with fewer breast cancer tissues (about 20–70% depending on the assay conditions) and it reacts with the fewest normal tissues of any of the antibodies. 520C9 reacts with kidney tubules (as do many monoclonal antibodies), but not pancreas, esophagus, lung, colon, stomach, brain, tonsil, liver, heart, ovary, skin, bone, uterus, bladder, or normal breast among some of the tissues tested.

2. Preparation of cDNA Library Encoding 520C9 Antibody

Polyadenylated RNA was isolated from approximately $1 \times 10^8$ (520C9 hybridoma) cells using the "FAST TRACK" mRNA isolation kit from Invitrogen (San Diego, Calif.). The presence of immunoglobulin heavy chain RNA was confirmed by Northern analysis (Molecular Cloning, 1989, Sambrook et al., eds., 2d ed., Cold Spring Harbor Laboratory Press, NY) using a recombinant probe containing the various J regions of heavy chain genomic DNA. Using 6 µg RNA for each, cDNA was prepared using the Invitrogen cDNA synthesis system with either random and oligo dT primers. Following synthesis, the cDNA was size-selected by isolating 0.5–3.0 Kilobase (Kb) fragments following agarose gel electrophoresis. After optimizing the cDNA to vector ratio, these fragments were then ligated to the pcDNA II Invitrogen cloning vector.

3. Isolation of $V_H$ and $V_L$ Domains

After transformation of the bacteria with plasmid library DNA, colony hybridization was performed using antibody constant (C) region and joining (J) region probes for either light or heavy chain genes. See Orlandi, R., et al., 1989, Proc. Nat. Aca. Sci. 86:3833. The antibody constant region probe can be obtained from any of light or heavy chain nucleotide sequences from an immunoglobulin gene using known procedures. Several potential positive clones were identified for both heavy and light chain genes and, after purification by a second round of screening, these were sequenced. One clone (M207) contained the sequence of non-functional Kappa chain which has a tyrosine substituted for a conserved cysteine, and also terminates prematurely due to a 4 base deletion which causes a frame-shift mutation in the variable-J region junction. A second light chain clone (M230) contained virtually the entire 520C9 light chain gene except for the last 18 amino acids of the constant region and approximately half of the signal sequence. The 520C9 heavy chain variable region was present on a clone of approximately 1,100 base pairs (F320) which ended near the end of the CH2 domain.

4. Mutagenesis of $V_H$ AND $V_L$

In order to construct the sFv, both the heavy and light chain variable regions were mutagenized to insert appropriate restriction sites (Kunkel, T. A., 1985, Proc. Nat. Acad. Sci. USA 82:1373). The heavy chain clone (F320) was mutagenized to insert a BamH1 site at the 5' end of $V_H$ (F321). The light chain was also mutagenized simultaneously by inserting an EcoRI site at the 5' end and a PstI site with a translation stop codon at the 3' end of the variable region (M231).

5. Sequencing cDNA clones encoding light and heavy chain were sequenced using external standard pUC primers and several specific internal primers which were prepared on the basis of the sequences obtained for the heavy chain. The nucleotide sequences were analyzed in a Genbank homology search (program Mucscan of DNA-star) to eliminate endogenous immunoglobulin genes. Translation into amino acids was checked with amino acid sequences in the NIH atlas edited by E. Kabat.

Amino acid sequences derived from 520C9 immunoglobulin confirmed the identity of these $V_H$ and $V_L$ cDNA clones. The heavy chain clone pF320 started 6 nucleotides upstream of the first ATG codon and extended into the CH2-encoding region, but it lacked the last nine amino acid codons of the CH2 constant domain and all of the CH3 coding region, as well as the 3' untranslated region and the poly A tail. Another short heavy chain clone containing only the CH2 and CH3 coding regions, and the poly A tail was initially assumed to represent the missing part of the 520C9 heavy chain. However, overlap between both sequences was not identical. The 520C9 clone (pF320) encodes the CH1 and CH2 domains of murine IgG1, whereas the short clone pF315 encodes the CH2 and CH3 of IgG2b.

6. Gene Design

A nucleic acid sequence encoding a composite 520C9 sFv region containing a single-chain Fv binding site which recognizes c-erbB-2 related tumor antigens was designed with the aid of Compugene software. The gene contains nucleic acid sequences encoding the $V_H$ and $V_L$ regions of the 520C9 antibody described above linked together with a double-stranded synthetic oligonucleotide coding for a peptide with the amino acid sequence set forth in the Sequence Listing as amino acid residue numbers 116 through 133 in SEQ ID NOS:3 and 4. This linker oligonucleotide contains helper cloning sites EcoRI and BamHI, and was designed to contain the assembly sites SacI and AatII near its 5' and 3' ends, respectively. These sites enable match-up and ligation to the 3' and 5' ends of 520C9 $V_H$ and $V_L$, respectively, which also contain these sites ($V_H$-linker-$V_L$). However, the order of linkage to the oligonucleotide may be reversed ($V_L$-linker-$V_H$) in this or any sFv of the invention. Other restriction sites were designed into the gene to provide alternative assembly sites. A sequence encoding the FB fragment of protein A was used as a leader.

The invention also embodies a humanized single-chain Fv, i.e., containing human framework sequences and CDR sequences which specify c-erbB-2 binding, e.g., like the CDRs of the 520C9 antibody. The humanized Fv is thus capable of binding c-erbB-2 while eliciting little or no immune response when administered to a patient. A nucleic acid sequence encoding a humanized sFv may be designed and constructed as follows. Two strategies for sFv design are especially useful. A homology search in the GenBank database for the most related human framework (FR) regions may be performed and FR regions of the sFv may be mutagenized according to sequences identified in the search to reproduce the corresponding human sequence; or information from computer modeling based on x-ray structures of model Fab fragments may be used (Amit et al., 1986, Science 233:747–753; Colman et al., 1987, Nature 326:358–363; Sheriff et al., 1987, Proc. Nat. Aca. Sci., 84:8075–8079; and Satow et al., 1986, J. Mol. Biol. 190:593–604, all of which are hereby incorporated by reference). In a preferred case, the most homologous human $V_H$ and $V_L$ sequences may be selected from a collection of PCR-cloned human V regions. The FRs are made synthetically and fused to CDRs to make successively more complete V regions by PCR-based ligation, until the full humanized $V_L$ and $V_H$ are completed. For example, a humanized sFv that is a hybrid of the murine 520C9 antibody CDRs and the human myeloma protein NEW FRs can be designed such that each variable region has the murine binding site within a human framework (FR1-CDR1-FR2-CDR2-FR3-CDR3-FR4). The Fab NEW crystal structure (Saul et al., 1978, J. Biol. Chem. 253:585–597) also may be used to predict the location of FRs in the variable regions. Once these regions are predicted, the amino acid sequence or the corresponding nucleotide sequence of the regions may be determined, and the sequences may be synthesized and cloned into shuttle plasmids, from which they may be further assembled and cloned into an expression plasmid; alternatively, the FR sequences of the 520C9 sFv may be mutagenized directly and the changes verified by supercoil sequencing with internal primers (Chen et al., 1985, DNA 4:165–170).

7. Preparation of and Purification 520C9 sFv

A. Inclusion Body Solubilization

The 520C9 sFv plasmid, based on a $T_7$ promoter and vector, was made by direct expression in *E. coli* of the fused gene sequence set forth in the Sequence Listing as SEQ. ID NO:3. Inclusion bodies (15.8 g) from a 2.0 liter fermentation were washed with 25 mM Tris, 10 mM EDTA, pH 8.0 (TE), plus 1M guanidine hydrochloride (GuHCl). The inclusion bodies were solubilized in TE, 6M GuHCl, 10 mM dithiothreitol (DTT), pH 9.0, and yielded 3825 $A_{280}$ units of material. This material was ethanol precipitated, washed with TE, 3M urea, then resuspended in TE, 8M urea, 10 mM DTT, pH 8.0. This precipitation step prepared the protein for ion exchange purification of the denatured sFv.

B. Ion Exchange Chromatography

The solubilized inclusion bodies were subjected to ion exchange chromatography in an effort to remove contaminating nucleic acids and *E. coli* proteins before renaturation of the sFv. The solubilized inclusion bodies in 8M urea were diluted with TE to a final urea concentration of 6M, then passed through 100 ml of DEAE-Sepharose Fast Flow in a radial flow column. The sFv was recovered in the unbound fraction (69% of the starting sample).

The pH of this sFv solution ($A_{280}$=5.7; 290 ml) was adjusted to 5.5 with 1M acetic acid to prepare it for application to an S-Sepharose Fast Flow column. When the pH went below 6.0, however, precipitate formed in the sample. The sample was clarified; 60% of the sample was in the pellet and 40% in the supernatant. The supernatant was passed through 100 ml S-Sepharose Fast Flow and the sFv recovered in the unbound fraction. The pellet was resolubilized in TE, 6M GuHCl, 10 mM DTT, pH 9.0, and was also found to contain primarily sFv in a pool of 45 ml volume with an absorbance at 280 nm of 20 absorbance units. This reduced sFv pool was carried through the remaining steps of the purification.

C. Renaturation of sFv

Renaturation of the sFv was accomplished using a disulfide-restricted refolding approach, in which the disulfides were oxidized while the sFv was fully denatured, followed by removal of the denaturant and refolding. Oxidation of the sFv samples was carried out in TE, 6M GuHCl, 1 mM oxidized glutathione (GSSG), 0.1 mM reduced glutathione (GSH), pH 9.0. The sFv was diluted into the oxidation buffer to a final protein $A_{280}$=0.075 with a volume of 4000 ml and incubated overnight at room temperature. After overnight oxidation this solution was dialyzed against 10 mM sodium phosphate, 1 mM EDTA, 150 mM NaCl, 500 mM urea, pH 8.0 (PENU) [4×(20 liters×24 hrs)]. Low levels of activity were detected in the refolded sample.

D. Membrane Fractionation and Concentration of Active sFv

In order to remove aggregated misfolded material before any concentration step, the dialyzed refolded 520C9 sFv (5050 ml) was filtered through a 100K MWCO membrane (100,000 mol. wt. cut-off) (4×60 $cm^2$) using a Minitan ultrafiltration device (Millipore). This step required a considerable length of time (9 hours), primarily due to formation of precipitate in the retentate and membrane fouling as the protein concentration in the retentate increased. 95% of the protein in the refolded sample was retained by the 100K membranes, with 79% in the form of insoluble material. The 100K retentate had very low activity and was discarded.

The 100K filtrate contained most of the soluble sFv activity for binding c-erbB-2, and it was next concentrated using 10K MWCO membranes (10,000 mol. wt. cut-off) (4×60 $cm^2$) in the Minitan, to a volume of 100 ml (50×). This material was further concentrated using a YM10 10K MWCO membrane in a 50 ml Amicon stirred cell to a final volume of 5.2 ml (1000×). Only a slight amount of precipitate formed during the two 10K concentration steps. The specific activity of this concentrated material was significantly increased relative to the initial dialyzed refolding.

E. Size Exclusion Chromatography of Concentrated sFv

When refolded sFv was fractionated by size exclusion chromatography, all 520C9 sFv activity was determined to elute at the position of folded monomer. In order to enrich for active monomers, the 1000× concentrated sFv sample was fractionated on a Sephacryl S-200 HR column (2.5×40 cm) in PBSA (2.7 mM KCl, 1.1 mM $KH_2PO_4$, 138 mM NaCl, 8.1 mM $Na_2HPO_4.7H_2O$, 0.02% $NaN_3$)+0.5M urea. The elution profile of the column and SDS-PAGE analysis of the fractions showed two sFv monomer peaks. The two sFv monomer peak fractions were pooled (10 ml total) and displayed c-erbB-2 binding activity in competition assays.

F. Affinity Purification of 520C9 sFv

The extracellular domain of (ECD) c-erbB-2 was expressed in bacculovirus-infected insect cells. This protein (ECD c-erbB-2) was immobilized on an agarose affinity matrix. The sFv monomer peak was dialyzed against PBSA to remove the urea and then applied to a 0.7×4.5 cm ECD c-erbB-2-agarose affinity column in PBSA. The column was washed to baseline $A_{280}$, then eluted with PBSA+3M LiCl, pH=6.1. The peak fractions were pooled (4 ml) and dialyzed against PBSA to remove the LiCl. 72 μg of purified sFv was obtained from 750 μg of S-200 monomer fractions. Activity measurements on the column fractions were determined by a competitive assay. Briefly, sFv affinity purification fractions and HRP-conjugated 520C9 Fab fragments were allowed to compete for binding to SK-BR-3 membranes. Successful binding of the sFv preparation prevented the HRP-520C9 Fab fragment from binding to the membranes, thus also reducing or preventing utilization of the HRP substrate, and no color development (see below for details of competition assay). The results showed that virtually all of the sFv activity was bound by the column and was recovered in the eluted peak (FIG. 7). As expected, the specific activity of the eluted peak was increased relative to the column sample, and appeared to be essentially the same as the parent Fab control, within the experimental error of these measurements.

9. Yield After Purification

Table I shows the yield of various 520C9 preparations during the purification process. Protein concentration (μg/ml) was determined by the BioRad protein assay. Under "Total Yield", 300 AU denatured sFv stock represents 3.15 g inclusion bodies from 0.4 liters fermentation. The oxidation buffer was 25 mM Tris, 10 mM EDTA, 6M GdnHCl, 1 MM GSSG, 0.1 mM GSH, pH 9.0. Oxidation was performed at room temperature overnight. Oxidized sample was dialyzed against 10 mM sodium phosphate, 1 mM EDTA, 150 mM NaCl, 500 mM urea, pH 8.0. All subsequent steps were carried out in this buffer, except for affinity chromatography, which was carried out in PBSA.

TABLE I

| Sample | Volume | Protein Concentration | Total Yield | % Yield |
|---|---|---|---|---|
| 1. Refolding III (oxidation) | 4000 ml | 0.075 $A_{280}$ | 300 AU | — |
| 2. Dialyzed Refolding III | 5050 ml | 38 μg/ml | 191.9 mg | 100 |
| 3. Minitan 100 K Filtrate | 5000 ml | 2 μg/ml | 10.0 mg | 5.4 |
| 4. Minitan 10K Retentate | 100 ml | 45 μg/ml | 4.5 mg | 2.3 |
| 6. YM10 10K Retentate | 5.2 ml | 600 μg/ml | 3.1 mg | 1.6 |
| 7. S-200 sFv Monomer Peak | 10.0 ml | 58 μg/ml | 0.58 mg | 0.3 |
| 8. Affinity Purified sFv | 5.5 ml | 13 μg/ml | 0.07 mg | 0.04 |

10. Immunotoxin Construction

Figure 8:
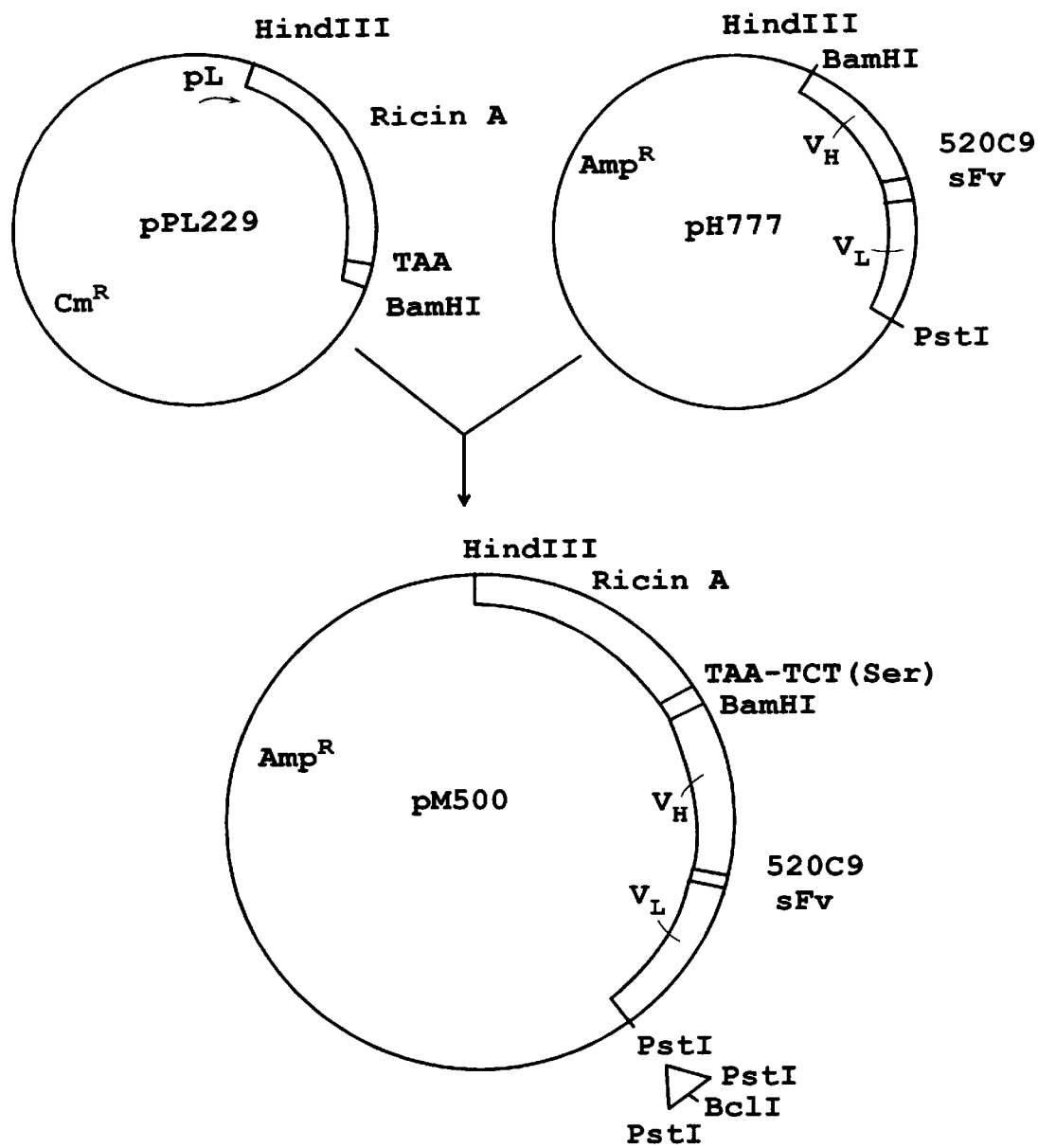
FIG. 8 is a diagrammatic representation of the construction of a plasmid encoding the 520C9 sFv-ricin A fused immunotoxin gene.

The ricin A-520C9 single chain fused immunotoxin (SEQ. ID NO:7) encoding gene was constructed by isolating the gene coding for ricin A on a HindIII to BamH1 fragment from pPL229 (Cetus Corporation, Emeryville, Calif.) and using it upstream of the 520C9 sFv in pH777, as shown in FIG. 8. This fusion contains the 122 amino acid natural linker present between the A and B domains of ricin. However, in the original pRAP229 expression vector the codon for amino acid 268 of ricin was converted to a TAA translation stop codon so that the expression of the resulting gene produces only ricin A. Therefore, in order to remove the translation stop codon, site-directed mutagenesis was performed to remove the TAA and restore the natural serine codon. This then allows translation to continue through the entire immunotoxin gene.

In order to insert the immunotoxin back into the pPL229 and pRAP229 expression vectors, the PstI site at the end of the immunotoxin gene had to be converted to a sequence that was compatible with the BamHI site in vector. A synthetic oligonucleotide adaptor containing a BclI site nested between PstI ends was inserted. BclI and BamHI ends are compatible and can be combined into a hybrid BclI/BamHI site. Since BclI nuclease is sensitive to dam methylation, the construction first was transformed into a dam(-) E. coli strain, Gm48, in order to digest the plasmid DNA with BclI (and HindIII), then insert the entire immunotoxin gene on a HindIII/BclI fragment back into both Hind III/BamHI-digested expression vectors.

When native 520C9 IgG1 is conjugated with native ricin A chain or recombinant ricin A chain, the resulting immunotoxin is able to inhibit protein synthesis by 50% at a concentration of about $0.4 \times 10^{-9}$M against SK-Br-3 cells. In addition to reacting with SK-Br-3 breast cancer cells, native 520C9 IgG1 immunotoxin also inhibits an ovarian cancer cell line, OVCAR-3, with a $ID_{50}$ of $2.0 \times 10^{-9}$M.

In the ricin A-sFv fusion protein described above, ricin acts as leader for expression, i.e., is fused to the amino terminus of sFv. Following direct expression, soluble protein was shown to react with antibodies against native 520C9 Fab and also to exhibit ricin A chain enzymatic activity.

In another design, the ricin A chain is fused to the carboxy terminus of sFv. The 520C9 sFv may be secreted via the PelB signal sequence with ricin A chain attached to the C-terminus of sFv. For this construct, sequences encoding the PelB-signal sequence, sFv, and ricin are joined in a bluescript plasmid via a HindIII site directly following sFv (in our expression plasmids) and the HindIII site preceding the ricin gene, in a three part assembly (RI-HindIII-BamHI). A new PstI site following the ricin gene is obtained via the Bluescript polylinker. Mutagenesis of this DNA removes the stop codon and the original PstI site at the end of sFv, and places several serine residues between the sFv and ricin genes. This new gene fusion, PelB signal sequence/sFv/ricin A, can be inserted into expression vectors as an EcoRI/PstI fragment.

In another design, the pseudomonas exotoxin fragment analogous to ricin A chain, PE40, is fused to the carboxy terminus of the anti-c-erbB-2 741F8 sFv (Seq ID NOS: 15 and 16). The resulting 741F8 sFv-PE40 is a single-chain Fv-toxin fusion protein, which was constructed with an 18 residue short FB leader which initially was left on the protein. E. coli expression of this protein produced inclusion bodies that were refolded in a 3M urea glutathione/redox buffer. The resulting sFv-PE40 was shown to specifically kill c-erbB-2 bearing cells in culture more fully and with apparently better cytotoxicity than the corresponding crosslinked immunotoxin. The sFv-toxin protein, as well as the 741F8 sFv, can be made in good yields by these procedures, and may be used as therapeutic and diagnostic agents for tumors bearing the c-erbB-2 or related antigens, such as breast and ovarian cancer.

11. Assays

A. Competition ELISA

SK-Br-3 extract is prepared as a source of c-erbB-2 antigen as follows. SK-Br-3 breast cancer cells (Ring et al. 1989, Cancer Research 49:3070–3080), are grown to near confluence in Iscove's medium (Gibco BRL, Gaithersburg, Md.) plus 5% fetal bovine serum and 2 mM glutamine. The medium is aspirated, and the cells are rinsed with 10 ml fetal bovine serum (FBS) plus calcium and magnesium. The cells are scraped off with a rubber policeman into 10 ml FBS plus calcium and magnesium, and the flask is rinsed out with another 5 ml of this buffer. The cells are then centrifuged at 100 rpm. The supernate is aspirated off, and the cells are resuspended at $10^7$ cells/ml in 10 mM NaCl, 0.5% NP40, pH 8 (TNN buffer), and are pipetted up and down to dissolve the pellet. The solution is then centrifuged at 1000 rpm to remove nuclei and other insoluble debris. The extract is filtered through 0.45 Millex HA and 0.2 Millex Gv filters. The TNN extract is stored as aliquots in Wheaton freezing vials at −70° C.

A fresh vial of SK-Br-3 TNN extract is thawed and diluted 200-fold into deionized water. Immediately thereafter, 40 ug per well are added to a Dynatech PVC 96 well plak, which is allowed to sit overnight in a 37° C. dry incubator. The plates are washed four times in phosphate buffered saline (PBS), 1% skim milk, 0.05% Tween 20.

The non-specific binding sites are blocked as follows. When the plate is dry, 100 ug per well PBS is added containing 1% skim milk, and the incubation allowed to proceed for one hour at room temperature.

The single-chain Fv test samples and standard 520C9 whole antibody dilutions are then added as follows. 520C9 antibody and test samples are diluted in dilution buffer (PBS+1% skim milk) in serial two-fold steps, initially at 50 ug/ml and making at least 10 dilutions for 520C9 standards. A control containing only dilution buffer is included. The diluted samples and standards are added at 50 ul per well and incubated for 30 minutes at room temperature.

The 520C9-horseradish peroxidase (HRP) probe is added as follows. 520C9-HRP conjugate (Zymed Labs., South San Francisco, Calif.) is diluted to 14 ug/ml with 1% skim milk in dilution buffer. The optimum dilutions must be determined for each new batch of peroxidase conjugate without removing the previous steps. 20 ul per well of probe was added and incubated for one hour at room temperature. The plate is then washed four times in PBS. The peroxidase substrate is then added. The substrate solution should be made fresh for each use by diluting tetramethyl benzidine stock (TMB; 2 mg/ml in 100% ethanol) 1:20 and 3% hydrogen peroxide stock 1:2200 in substrate buffer (10 mM sodium acetate, 10 mM Na, EDTA, pH 5.0). This is incubated for 30 minutes at room temperature. The wells are then quenched with 100 ul per well 0.8M $H_2SO_4$ and the absorbance at 150 nm read.

Figure 9:
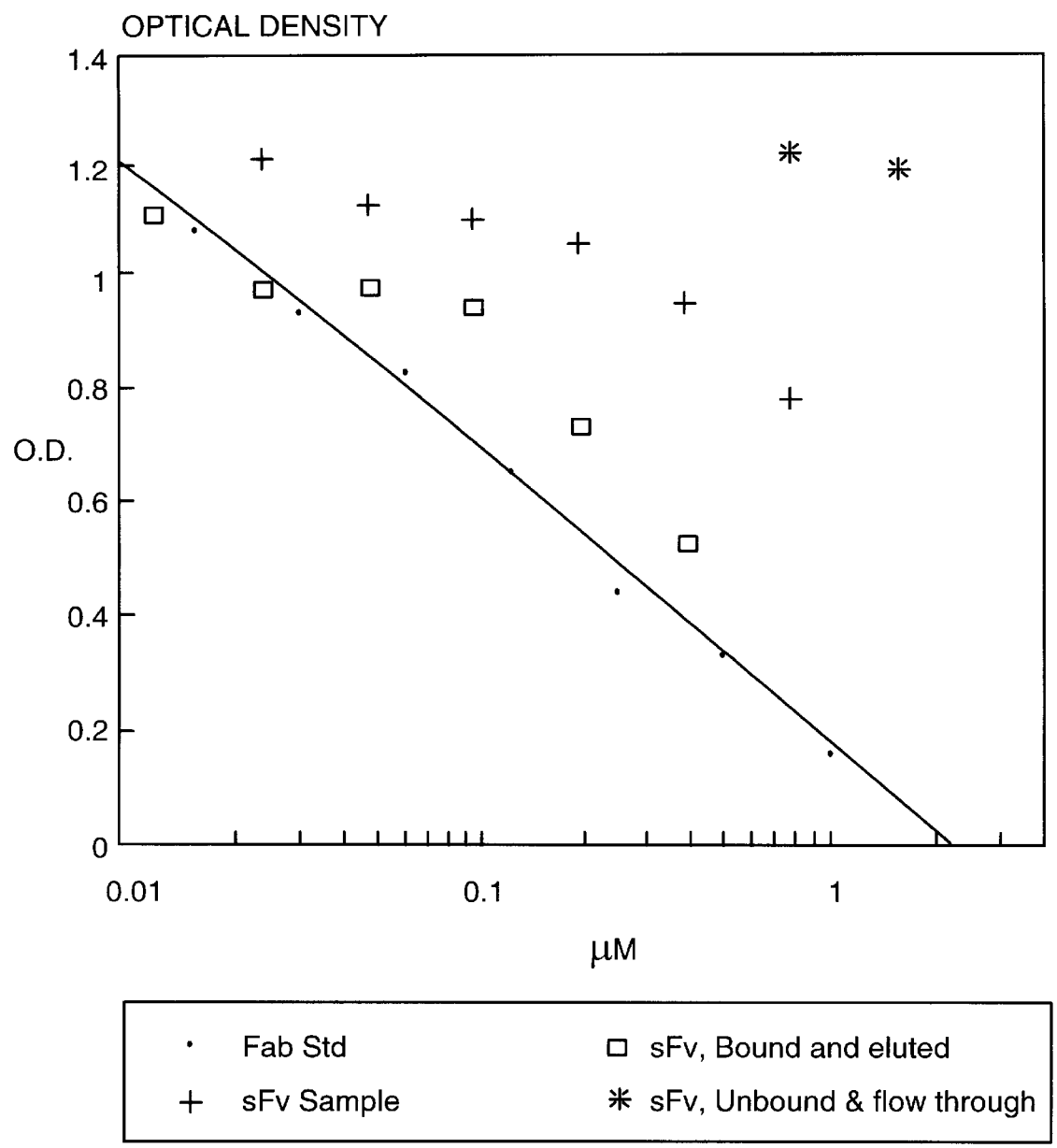
FIG. 9 is a graphic representation of the results of a competition assay comparing the c-erbB-2 binding activity of the 520C9 monoclonal antibody (specific for c-erbB-2), an Fab fragment of that monoclonal antibody (filled dots), and different affinity purified fractions of the single-chain-Fv binding site for c-erbB-2 constructed from the variable regions of the 520C9 monoclonal antibody (sFv whole sample (+), sFv bound and eluted from a column of immobilized extracellular domain of C-erbB-2 (squares) and sFv flow-through (unbound, *)).

FIG. 9 compares the binding ability of the parent refolded but unpurified 520C9 monoclonal antibody, 520C9 Fab fragments, and the 520C9 sFv single-chain binding site after binding and elution from an affinity column (eluted) or the unbound flow through fraction (passed). In FIG. 9, the fully purified 520C9 sFv exhibits an affinity for c-erbB-2 that is indistinguishable from the parent monoclonal antibody, within the error of measuring protein concentration.

B. In vivo Testing

Immunotoxins that are strong inhibitors of protein synthesis against breast cancer cells grown in culture may be tested for their in vivo efficacy. The in vivo assay is typically done in a nude mouse model using xenografts of human MX-1 breast cancer cells. Mice are injected with either PBS (control) or different concentrations of sFv-toxin immunotoxin, and a concentration-dependent inhibition of tumor growth will be observed. It is expected that higher doses of immunotoxin will produce a better effect.

The invention may be embodied in other specific forms without departing from the spirit and scope thereof. The present embodiments are therefore to be considered in all respects as illustrative and not restrictive, the scope of the invention being indicated by the appended claims rather than by the foregoing description, and all changes which come within the meaning and range of equivalence of the claims are intended to be embraced therein.

We claim:

1. A DNA molecule comprising nucleotide residue numbers 1–729 of SEQ ID NO: 3.

2. A method of producing a single chain polypeptide having binding specificity for a c-erbB-2-related tumor antigen, said method comprising the steps of:

(a) transfecting the DNA molecule of claim 1 into a host cell to produce a transformant; and
(b) culturing said transformant to produce said single-chain polypeptide.

3. A host cell transfected with the DNA molecule of claim 1.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 3768 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..3768
        ( D ) OTHER INFORMATION: /note= "product = "cerB-b2""

( x i ) SEQUENCE DESCRIPTION: SEQ ID NO:1:

```
ATG  GAG  CTG  GCG  GCC  TTG  TGC  CGC  TGG  GGG  CTC  CTC  CTC  GCC  CTC  TTG         4 8
Met  Glu  Leu  Ala  Ala  Leu  Cys  Arg  Trp  Gly  Leu  Leu  Leu  Ala  Leu  Leu
```

```
  1                     5                         10                        15
CCC  CCC  GGA  GCC  GCG  AGC  ACC  CAA  GTG  TGC  ACC  GGC  ACA  GAC  ATG  AAG        96
Pro  Pro  Gly  Ala  Ala  Ser  Thr  Gln  Val  Cys  Thr  Gly  Thr  Asp  Met  Lys
               20                   25                   30

CTG  CGG  CTC  CCT  GCC  AGT  CCC  GAG  ACC  CAC  CTG  GAC  ATG  CTC  CGC  CAC       144
Leu  Arg  Leu  Pro  Ala  Ser  Pro  Glu  Thr  His  Leu  Asp  Met  Leu  Arg  His
               35                   40                   45

CTC  TAC  CAG  GGC  TGC  CAG  GTG  GTG  CAG  GGA  AAC  CTG  GAA  CTC  ACC  TAC       192
Leu  Tyr  Gln  Gly  Cys  Gln  Val  Val  Gln  Gly  Asn  Leu  Glu  Leu  Thr  Tyr
          50                        55                        60

CTG  CCC  ACC  AAT  GCC  AGC  CTG  TCC  TTC  CTG  CAG  GAT  ATC  CAG  GAG  GTG       240
Leu  Pro  Thr  Asn  Ala  Ser  Leu  Ser  Phe  Leu  Gln  Asp  Ile  Gln  Glu  Val
65                       70                   75                        80

CAG  GGC  TAC  GTG  CTC  ATC  GCT  CAC  AAC  CAA  GTG  AGG  CAG  GTC  CCA  CTG       288
Gln  Gly  Tyr  Val  Leu  Ile  Ala  His  Asn  Gln  Val  Arg  Gln  Val  Pro  Leu
                    85                   90                        95

CAG  AGG  CTG  CGG  ATT  GTG  CGA  GGC  ACC  CAG  CTC  TTT  GAG  GAC  AAC  TAT       336
Gln  Arg  Leu  Arg  Ile  Val  Arg  Gly  Thr  Gln  Leu  Phe  Glu  Asp  Asn  Tyr
               100                       105                  110

GCC  CTG  GCC  GTG  CTA  GAC  AAT  GGA  GAC  CCG  CTG  AAC  AAT  ACC  ACC  CCT       384
Ala  Leu  Ala  Val  Leu  Asp  Asn  Gly  Asp  Pro  Leu  Asn  Asn  Thr  Thr  Pro
               115                       120                  125

GTC  ACA  GGG  GCC  TCC  CCA  GGA  GGC  CTG  CGG  GAG  CTG  CAG  CTT  CGA  AGC       432
Val  Thr  Gly  Ala  Ser  Pro  Gly  Gly  Leu  Arg  Glu  Leu  Gln  Leu  Arg  Ser
          130                       135                  140

CTC  ACA  GAG  ATC  TTG  AAA  GGA  GGG  GTC  TTG  ATC  CAG  CGG  AAC  CCC  CAG       480
Leu  Thr  Glu  Ile  Leu  Lys  Gly  Gly  Val  Leu  Ile  Gln  Arg  Asn  Pro  Gln
145                      150                       155                       160

CTC  TGC  TAC  CAG  GAC  ACG  ATT  TTG  TGG  AAG  GAC  ATC  TTC  CAC  AAG  AAC       528
Leu  Cys  Tyr  Gln  Asp  Thr  Ile  Leu  Trp  Lys  Asp  Ile  Phe  His  Lys  Asn
                    165                       170                  175

AAC  CAG  CTG  GCT  CTC  ACA  CTG  ATA  GAC  ACC  AAC  CGC  TCT  CGG  GCC  TGC       576
Asn  Gln  Leu  Ala  Leu  Thr  Leu  Ile  Asp  Thr  Asn  Arg  Ser  Arg  Ala  Cys
               180                       185                  190

CAC  CCC  TGT  TCT  CCG  ATG  TGT  AAG  GGC  TCC  CGC  TGC  TGG  GGA  GAG  AGT       624
His  Pro  Cys  Ser  Pro  Met  Cys  Lys  Gly  Ser  Arg  Cys  Trp  Gly  Glu  Ser
          195                       200                  205

TCT  GAG  GAT  TGT  CAG  AGC  CTG  ACG  CGC  ACT  GTC  TGT  GCC  GGT  GGC  TGT       672
Ser  Glu  Asp  Cys  Gln  Ser  Leu  Thr  Arg  Thr  Val  Cys  Ala  Gly  Gly  Cys
     210                       215                       220

GCC  CGC  TGC  AAG  GGG  CCA  CTG  CCC  ACT  GAC  TGC  TGC  CAT  GAG  CAG  TGT       720
Ala  Arg  Cys  Lys  Gly  Pro  Leu  Pro  Thr  Asp  Cys  Cys  His  Glu  Gln  Cys
225                      230                       235                       240

GCT  GCC  GGC  TGC  ACG  GGC  CCC  AAG  CAC  TCT  GAC  TGC  CTG  GCC  TGC  CTC       768
Ala  Ala  Gly  Cys  Thr  Gly  Pro  Lys  His  Ser  Asp  Cys  Leu  Ala  Cys  Leu
               245                       250                  255

CAC  TTC  AAC  CAC  AGT  GGC  ATC  TGT  GAG  CTG  CAC  TGC  CCA  GCC  CTG  GTC       816
His  Phe  Asn  His  Ser  Gly  Ile  Cys  Glu  Leu  His  Cys  Pro  Ala  Leu  Val
               260                       265                  270

ACC  TAC  AAC  ACA  GAC  ACG  TTT  GAG  TCC  ATG  CCC  AAT  CCC  GAG  GGC  CGG       864
Thr  Tyr  Asn  Thr  Asp  Thr  Phe  Glu  Ser  Met  Pro  Asn  Pro  Glu  Gly  Arg
               275                       280                  285

TAT  ACA  TTC  GGC  GCC  AGC  TGT  GTG  ACT  GCC  TGT  CCC  TAC  AAC  TAC  CTT       912
Tyr  Thr  Phe  Gly  Ala  Ser  Cys  Val  Thr  Ala  Cys  Pro  Tyr  Asn  Tyr  Leu
     290                       295                       300

TCT  ACG  GAC  GTG  GGA  TCC  TGC  ACC  CTC  GTC  TGC  CCC  CTG  CAC  AAC  CAA       960
Ser  Thr  Asp  Val  Gly  Ser  Cys  Thr  Leu  Val  Cys  Pro  Leu  His  Asn  Gln
305                      310                       315                       320

GAG  GTG  ACA  GCA  GAG  GAT  GGA  ACA  CAG  CGG  TGT  GAG  AAG  TGC  AGC  AAG      1008
Glu  Val  Thr  Ala  Glu  Asp  Gly  Thr  Gln  Arg  Cys  Glu  Lys  Cys  Ser  Lys
```

| | | | | | | | | | | | | | | | | |
|---|---|---|---|---|---|---|---|---|---|---|---|---|---|---|---|---|
| | | | | | 325 | | | | | 330 | | | | | 335 | |
| CCC | TGT | GCC | CGA | GTG | TGC | TAT | GGT | CTG | GGC | ATG | GAG | CAC | TTG | CGA | GAG | 1056 |
| Pro | Cys | Ala | Arg 340 | Val | Cys | Tyr | Gly | Leu 345 | Gly | Met | Glu | His | Leu 350 | Arg | Glu | |
| GTG | AGG | GCA | GTT | ACC | AGT | GCC | AAT | ATC | CAG | GAG | TTT | GCT | GGC | TGC | AAG | 1104 |
| Val | Arg | Ala 355 | Val | Thr | Ser | Ala | Asn 360 | Ile | Gln | Glu | Phe | Ala 365 | Gly | Cys | Lys | |
| AAG | ATC | TTT | GGG | AGC | CTG | GCA | TTT | CTG | CCG | GAG | AGC | TTT | GAT | GGG | GAC | 1152 |
| Lys | Ile 370 | Phe | Gly | Ser | Leu | Ala 375 | Phe | Leu | Pro | Glu | Ser 380 | Phe | Asp | Gly | Asp | |
| CCA | GCC | TCC | AAC | ACT | GCC | CCG | CTC | CAG | CCA | GAG | CAG | CTC | CAA | GTG | TTT | 1200 |
| Pro 385 | Ala | Ser | Asn | Thr | Ala 390 | Pro | Leu | Gln | Pro | Glu 395 | Gln | Leu | Gln | Val | Phe 400 | |
| GAG | ACT | CTG | GAA | GAG | ATC | ACA | GGT | TAC | CTA | TAC | ATC | TCA | GCA | TGG | CCG | 1248 |
| Glu | Thr | Leu | Glu | Glu 405 | Ile | Thr | Gly | Tyr | Leu 410 | Tyr | Ile | Ser | Ala | Trp 415 | Pro | |
| GAC | AGC | CTG | CCT | GAC | CTC | AGC | GTC | TTC | CAG | AAC | CTG | CAA | GTA | ATC | CGG | 1296 |
| Asp | Ser | Leu | Pro 420 | Asp | Leu | Ser | Val | Phe 425 | Gln | Asn | Leu | Gln | Val 430 | Ile | Arg | |
| GGA | CGA | ATT | CTG | CAC | AAT | GGC | GCC | TAC | TCG | CTG | ACC | CTG | CAA | GGG | CTG | 1344 |
| Gly | Arg | Ile 435 | Leu | His | Asn | Gly | Ala 440 | Tyr | Ser | Leu | Thr | Leu 445 | Gln | Gly | Leu | |
| GGC | ATC | AGC | TGG | CTG | GGG | CTG | CGC | TCA | CTG | AGG | GAA | CTG | GGC | AGT | GGA | 1392 |
| Gly | Ile | Ser 450 | Trp | Leu | Gly | Leu | Arg 455 | Ser | Leu | Arg | Glu | Leu 460 | Gly | Ser | Gly | |
| CTG | GCC | CTC | ATC | CAC | CAT | AAC | ACC | CAC | CTC | TGC | TTC | GTG | CAC | ACG | GTG | 1440 |
| Leu | Ala | Leu | Ile 465 | His | His | Asn | Thr | His 470 | Leu | Cys | Phe | Val | His 475 | Thr | Val 480 | |
| CCC | TGG | GAC | CAG | CTC | TTT | CGG | AAC | CCG | CAC | CAA | GCT | CTG | CTC | CAC | ACT | 1488 |
| Pro | Trp | Asp | Gln | Leu 485 | Phe | Arg | Asn | Pro | His 490 | Gln | Ala | Leu | Leu | His 495 | Thr | |
| GCC | AAC | CGG | CCA | GAG | GAC | GAG | TGT | GTG | GGC | GAG | GGC | CTG | GCC | TGC | CAC | 1536 |
| Ala | Asn | Arg | Pro 500 | Glu | Asp | Glu | Cys | Val 505 | Gly | Glu | Gly | Leu | Ala 510 | Cys | His | |
| CAG | CTG | TGC | GCC | CGA | GGG | CAC | TGC | TGG | GGT | CCA | GGG | CCC | ACC | CAG | TGT | 1584 |
| Gln | Leu | Cys 515 | Ala | Arg | Gly | His | Cys 520 | Trp | Gly | Pro | Gly | Pro 525 | Thr | Gln | Cys | |
| GTC | AAC | TGC | AGC | CAG | TTC | CTT | CGG | GGC | CAG | GAG | TGC | GTG | GAG | GAA | TGC | 1632 |
| Val | Asn | Cys | Ser 530 | Gln | Phe | Leu | Arg | Gly 535 | Gln | Glu | Cys | Val | Glu 540 | Glu | Cys | |
| CGA | GTA | CTG | CAG | GGG | CTC | CCC | AGG | GAG | TAT | GTG | AAT | GCC | AGG | CAC | TGT | 1680 |
| Arg 545 | Val | Leu | Gln | Gly | Leu 550 | Pro | Arg | Glu | Tyr | Val 555 | Asn | Ala | Arg | His | Cys 560 | |
| TTG | CCG | TGC | CAC | CCT | GAG | TGT | CAG | CCC | CAG | AAT | GGC | TCA | GTG | ACC | TGT | 1728 |
| Leu | Pro | Cys | His | Pro 565 | Glu | Cys | Gln | Pro | Gln 570 | Asn | Gly | Ser | Val | Thr 575 | Cys | |
| TTT | GGA | CCG | GAG | GCT | GAC | CAG | TGT | GTG | GCC | TGT | GCC | CAC | TAT | AAG | GAC | 1776 |
| Phe | Gly | Pro | Glu 580 | Ala | Asp | Gln | Cys | Val 585 | Ala | Cys | Ala | His | Tyr 590 | Lys | Asp | |
| CCT | CCC | TTC | TGC | GTG | GCC | CGC | TGC | CCC | AGC | GGT | GTG | AAA | CCT | GAC | CTC | 1824 |
| Pro | Pro | Phe 595 | Cys | Val | Ala | Arg | Cys 600 | Pro | Ser | Gly | Val | Lys 605 | Pro | Asp | Leu | |
| TCC | TAC | ATG | CCC | ATC | TGG | AAG | TTT | CCA | GAT | GAG | GAG | GGC | GCA | TGC | CAG | 1872 |
| Ser | Tyr | Met | Pro | Ile 610 | Trp | Lys | Phe | Pro | Asp 615 | Glu | Glu | Gly | Ala | Cys 620 | Gln | |
| CCT | TGC | CCC | ATC | AAC | TGT | ACC | CAC | TCC | TGT | GTG | GAC | CTG | GAT | GAC | AAG | 1920 |
| Pro | Cys | Pro 625 | Ile | Asn | Cys | Thr | His 630 | Ser | Cys | Val | Asp | Leu 635 | Asp | Asp | Lys 640 | |
| GGC | TGC | CCC | GCC | GAG | CAG | AGA | GCC | AGC | CCT | CTG | ACG | TCC | ATC | ATC | TCT | 1968 |
| Gly | Cys | Pro | Ala | Glu | Gln | Arg | Ala | Ser | Pro | Leu | Thr | Ser | Ile | Ile | Ser | |

|  |  |  |  |  |  |  |  |  |  |  |  |  |  |  |  |
|---|---|---|---|---|---|---|---|---|---|---|---|---|---|---|---|
|  |  |  | 645 |  |  |  | 650 |  |  |  |  |  | 655 |  |  |
| GCG | GTG | GTT | GGC | ATT | CTG | CTG | GTC | GTG | GTC | TTG | GGG | GTG | GTC | TTT | GGG | 2016
| Ala | Val | Val | Gly | Ile | Leu | Leu | Val | Val | Val | Leu | Gly | Val | Val | Phe | Gly |
|  |  |  | 660 |  |  |  | 665 |  |  |  |  |  | 670 |  |  |
| ATC | CTC | ATC | AAG | CGA | CGG | CAG | CAG | AAG | ATC | CGG | AAG | TAC | ACG | ATG | CGG | 2064
| Ile | Leu | Ile | Lys | Arg | Arg | Gln | Gln | Lys | Ile | Arg | Lys | Tyr | Thr | Met | Arg |
|  |  |  | 675 |  |  |  | 680 |  |  |  |  |  | 685 |  |  |
| AGA | CTG | CTG | CAG | GAA | ACG | GAG | CTG | GTG | GAG | CCG | CTG | ACA | CCT | AGC | GGA | 2112
| Arg | Leu | Leu | Gln | Glu | Thr | Glu | Leu | Val | Glu | Pro | Leu | Thr | Pro | Ser | Gly |
|  |  |  | 690 |  |  |  | 695 |  |  |  |  |  | 700 |  |  |
| GCG | ATG | CCC | AAC | CAG | GCG | CAG | ATG | CGG | ATC | CTG | AAA | GAG | ACG | GAG | CTG | 2160
| Ala | Met | Pro | Asn | Gln | Ala | Gln | Met | Arg | Ile | Leu | Lys | Glu | Thr | Glu | Leu |
| 705 |  |  |  |  | 710 |  |  |  |  | 715 |  |  |  |  | 720 |
| AGG | AAG | GTG | AAG | GTG | CTT | GGA | TCT | GGC | GCT | TTT | GGC | ACA | GTC | TAC | AAG | 2208
| Arg | Lys | Val | Lys | Val | Leu | Gly | Ser | Gly | Ala | Phe | Gly | Thr | Val | Tyr | Lys |
|  |  |  |  | 725 |  |  |  |  | 730 |  |  |  |  | 735 |  |
| GGC | ATC | TGG | ATC | CCT | GAT | GGG | GAG | AAT | GTG | AAA | ATT | CCA | GTG | GCC | ATC | 2256
| Gly | Ile | Trp | Ile | Pro | Asp | Gly | Glu | Asn | Val | Lys | Ile | Pro | Val | Ala | Ile |
|  |  |  | 740 |  |  |  | 745 |  |  |  |  |  | 750 |  |  |
| AAA | GTG | TTG | AGG | GAA | AAC | ACA | TCC | CCC | AAA | GCC | AAC | AAA | GAA | ATC | TTA | 2304
| Lys | Val | Leu | Arg | Glu | Asn | Thr | Ser | Pro | Lys | Ala | Asn | Lys | Glu | Ile | Leu |
|  |  |  | 755 |  |  |  | 760 |  |  |  |  |  | 765 |  |  |
| GAC | GAA | GCA | TAC | GTG | ATG | GCT | GGT | GTG | GGC | TCC | CCA | TAT | GTC | TCC | CGC | 2352
| Asp | Glu | Ala | Tyr | Val | Met | Ala | Gly | Val | Gly | Ser | Pro | Tyr | Val | Ser | Arg |
| 770 |  |  |  |  | 775 |  |  |  |  | 780 |  |  |  |  |  |
| CTT | CTG | GGC | ATC | TGC | CTG | ACA | TCC | ACG | GTG | CAG | CTG | GTG | ACA | CAG | CTT | 2400
| Leu | Leu | Gly | Ile | Cys | Leu | Thr | Ser | Thr | Val | Gln | Leu | Val | Thr | Gln | Leu |
| 785 |  |  |  |  | 790 |  |  |  |  | 795 |  |  |  |  | 800 |
| ATG | CCC | TAT | GGC | TGC | CTC | TTA | GAC | CAT | GTC | CGG | GAA | AAC | CGC | GGA | CGC | 2448
| Met | Pro | Tyr | Gly | Cys | Leu | Leu | Asp | His | Val | Arg | Glu | Asn | Arg | Gly | Arg |
|  |  |  | 805 |  |  |  | 810 |  |  |  |  |  | 815 |  |  |
| CTG | GGC | TCC | CAG | GAC | CTG | CTG | AAC | TGG | TGT | ATG | CAG | ATT | GCC | AAG | GGG | 2496
| Leu | Gly | Ser | Gln | Asp | Leu | Leu | Asn | Trp | Cys | Met | Gln | Ile | Ala | Lys | Gly |
|  |  |  | 820 |  |  |  | 825 |  |  |  |  |  | 830 |  |  |
| ATG | AGC | TAC | CTG | GAG | GAT | GTG | CGG | CTC | GTA | CAC | AGG | GAC | TTG | GCC | GCT | 2544
| Met | Ser | Tyr | Leu | Glu | Asp | Val | Arg | Leu | Val | His | Arg | Asp | Leu | Ala | Ala |
|  |  |  | 835 |  |  |  | 840 |  |  |  |  |  | 845 |  |  |
| CGG | AAC | GTG | CTG | GTC | AAG | AGT | CCC | AAC | CAT | GTC | AAA | ATT | ACA | GAC | TTC | 2592
| Arg | Asn | Val | Leu | Val | Lys | Ser | Pro | Asn | His | Val | Lys | Ile | Thr | Asp | Phe |
| 850 |  |  |  |  | 855 |  |  |  |  | 860 |  |  |  |  |  |
| GGG | CTG | GCT | CGG | CTG | CTG | GAC | ATT | GAC | GAG | ACA | GAG | TAC | CAT | GCA | GAT | 2640
| Gly | Leu | Ala | Arg | Leu | Leu | Asp | Ile | Asp | Glu | Thr | Glu | Tyr | His | Ala | Asp |
| 865 |  |  |  |  | 870 |  |  |  |  | 875 |  |  |  |  | 880 |
| GGG | GGC | AAG | GTG | CCC | ATC | AAG | TGG | ATG | GCG | CTG | GAG | TCC | ATT | CTC | CGC | 2688
| Gly | Gly | Lys | Val | Pro | Ile | Lys | Trp | Met | Ala | Leu | Glu | Ser | Ile | Leu | Arg |
|  |  |  |  | 885 |  |  |  |  | 890 |  |  |  |  | 895 |  |
| CGG | CGG | TTC | ACC | CAC | CAG | AGT | GAT | GTG | TGG | AGT | TAT | GGT | GTG | ACT | GTG | 2736
| Arg | Arg | Phe | Thr | His | Gln | Ser | Asp | Val | Trp | Ser | Tyr | Gly | Val | Thr | Val |
|  |  |  | 900 |  |  |  |  |  | 905 |  |  |  |  | 910 |  |
| TGG | GAG | CTG | ATG | ACT | TTT | GGG | GCC | AAA | CCT | TAC | GAT | GGG | ATC | CCA | GCC | 2784
| Trp | Glu | Leu | Met | Thr | Phe | Gly | Ala | Lys | Pro | Tyr | Asp | Gly | Ile | Pro | Ala |
|  |  |  | 915 |  |  |  | 920 |  |  |  |  |  | 925 |  |  |
| CGG | GAG | ATC | CCT | GAC | CTG | CTG | GAA | AAG | GGG | GAG | CGG | CTG | CCC | CAG | CCC | 2832
| Arg | Glu | Ile | Pro | Asp | Leu | Leu | Glu | Lys | Gly | Glu | Arg | Leu | Pro | Gln | Pro |
|  |  |  | 930 |  |  |  | 935 |  |  |  |  |  | 940 |  |  |
| CCC | ATC | TGC | ACC | ATT | GAT | GTC | TAC | ATG | ATC | ATG | GTC | AAA | TGT | TGG | ATG | 2880
| Pro | Ile | Cys | Thr | Ile | Asp | Val | Tyr | Met | Ile | Met | Val | Lys | Cys | Trp | Met |
| 945 |  |  |  |  | 950 |  |  |  |  | 955 |  |  |  |  | 960 |
| ATT | GAC | TCT | GAA | TGT | CGG | CCA | AGA | TTC | CGG | GAG | TTG | GTG | TCT | GAA | TTC | 2928
| Ile | Asp | Ser | Glu | Cys | Arg | Pro | Arg | Phe | Arg | Glu | Leu | Val | Ser | Glu | Phe |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     |     | 965 |     |     |     |     | 970 |     |     |     |     | 975 |      |
| TCC | CGC | ATG | GCC | AGG | GAC | CCC | CAG | CGC | TTT | GTG | GTC | ATC | CAG | AAT | GAG | 2976 |
| Ser | Arg | Met | Ala | Arg | Asp | Pro | Gln | Arg | Phe | Val | Val | Ile | Gln | Asn | Glu |      |
|     |     |     | 980 |     |     |     | 985 |     |     |     |     |     | 990 |     |     |      |
| GAC | TTG | GGC | CCA | GCC | AGT | CCC | TTG | GAC | AGC | ACC | TTC | TAC | CGC | TCA | CTG | 3024 |
| Asp | Leu | Gly | Pro | Ala | Ser | Pro | Leu | Asp | Ser | Thr | Phe | Tyr | Arg | Ser | Leu |      |
|     |     | 995 |     |     |     |     | 1000|     |     |     |     | 1005|     |     |     |      |
| CTG | GAG | GAC | GAT | GAC | ATG | GGG | GAC | CTG | GTG | GAT | GCT | GAG | GAG | TAT | CTG | 3072 |
| Leu | Glu | Asp | Asp | Asp | Met | Gly | Asp | Leu | Val | Asp | Ala | Glu | Glu | Tyr | Leu |      |
|     |     | 1010|     |     |     |     | 1015|     |     |     |     | 1020|     |     |     |      |
| GTA | CCC | CAG | CAG | GGC | TTC | TTC | TGT | CCA | GAC | CCT | GCC | CCG | GGC | GCT | GGG | 3120 |
| Val | Pro | Gln | Gln | Gly | Phe | Phe | Cys | Pro | Asp | Pro | Ala | Pro | Gly | Ala | Gly |      |
| 1025|     |     |     |     |     | 1030|     |     |     |     | 1035|     |     |     | 1040|      |
| GGC | ATG | GTC | CAC | CAC | AGG | CAC | CGC | AGC | TCA | TCT | ACC | AGG | AGT | GGC | GGT | 3168 |
| Gly | Met | Val | His | His | Arg | His | Arg | Ser | Ser | Ser | Thr | Arg | Ser | Gly | Gly |      |
|     |     |     |     | 1045|     |     |     |     | 1050|     |     |     |     | 1055|     |      |
| GGG | GAC | CTG | ACA | CTA | GGG | CTG | GAG | CCC | TCT | GAA | GAG | GAG | GCC | CCC | AGG | 3216 |
| Gly | Asp | Leu | Thr | Leu | Gly | Leu | Glu | Pro | Ser | Glu | Glu | Glu | Ala | Pro | Arg |      |
|     |     |     | 1060|     |     |     |     | 1065|     |     |     |     | 1070|     |     |      |
| TCT | CCA | CTG | GCA | CCC | TCC | GAA | GGG | GCT | GGC | TCC | GAT | GTA | TTT | GAT | GGT | 3264 |
| Ser | Pro | Leu | Ala | Pro | Ser | Glu | Gly | Ala | Gly | Ser | Asp | Val | Phe | Asp | Gly |      |
|     |     | 1075|     |     |     |     | 1080|     |     |     |     | 1085|     |     |     |      |
| GAC | CTG | GGA | ATG | GGG | GCA | GCC | AAG | GGG | CTG | CAA | AGC | CTC | CCC | ACA | CAT | 3312 |
| Asp | Leu | Gly | Met | Gly | Ala | Ala | Lys | Gly | Leu | Gln | Ser | Leu | Pro | Thr | His |      |
|     |     | 1090|     |     |     |     | 1095|     |     |     |     | 1100|     |     |     |      |
| GAC | CCC | AGC | CCT | CTA | CAG | CGG | TAC | AGT | GAG | GAC | CCC | ACA | GTA | CCC | CTG | 3360 |
| Asp | Pro | Ser | Pro | Leu | Gln | Arg | Tyr | Ser | Glu | Asp | Pro | Thr | Val | Pro | Leu |      |
| 1105|     |     |     |     | 1110|     |     |     |     | 1115|     |     |     |     | 1120|      |
| CCC | TCT | GAG | ACT | GAT | GGC | TAC | GTT | GCC | CCC | CTG | ACC | TGC | AGC | CCC | CAG | 3408 |
| Pro | Ser | Glu | Thr | Asp | Gly | Tyr | Val | Ala | Pro | Leu | Thr | Cys | Ser | Pro | Gln |      |
|     |     |     |     | 1125|     |     |     |     | 1130|     |     |     |     | 1135|     |      |
| CCT | GAA | TAT | GTG | AAC | CAG | CCA | GAT | GTT | CGG | CCC | CAG | CCC | CCT | TCG | CCC | 3456 |
| Pro | Glu | Tyr | Val | Asn | Gln | Pro | Asp | Val | Arg | Pro | Gln | Pro | Pro | Ser | Pro |      |
|     |     |     |     | 1140|     |     |     |     | 1145|     |     |     |     | 1150|     |      |
| CGA | GAG | GGC | CCT | CTG | CCT | GCT | GCC | CGA | CCT | GCT | GGT | GCC | ACT | CTG | GAA | 3504 |
| Arg | Glu | Gly | Pro | Leu | Pro | Ala | Ala | Arg | Pro | Ala | Gly | Ala | Thr | Leu | Glu |      |
|     |     |     | 1155|     |     |     |     | 1160|     |     |     |     | 1165|     |     |      |
| AGG | CCC | AAG | ACT | CTC | TCC | CCA | GGG | AAG | AAT | GGG | GTC | GTC | AAA | GAC | GTT | 3552 |
| Arg | Pro | Lys | Thr | Leu | Ser | Pro | Gly | Lys | Asn | Gly | Val | Val | Lys | Asp | Val |      |
|     |     | 1170|     |     |     |     | 1175|     |     |     |     | 1180|     |     |     |      |
| TTT | GCC | TTT | GGG | GGT | GCC | GTG | GAG | AAC | CCC | GAG | TAC | TTG | ACA | CCC | CAG | 3600 |
| Phe | Ala | Phe | Gly | Gly | Ala | Val | Glu | Asn | Pro | Glu | Tyr | Leu | Thr | Pro | Gln |      |
| 1185|     |     |     |     | 1190|     |     |     |     | 1195|     |     |     |     | 1200|      |
| GGA | GGA | GCT | GCC | CCT | CAG | CCC | CAC | CCT | CCT | CCT | GCC | TTC | AGC | CCA | GCC | 3648 |
| Gly | Gly | Ala | Ala | Pro | Gln | Pro | His | Pro | Pro | Pro | Ala | Phe | Ser | Pro | Ala |      |
|     |     |     |     | 1205|     |     |     |     | 1210|     |     |     |     | 1215|     |      |
| TTC | GAC | AAC | CTC | TAT | TAC | TGG | GAC | CAG | GAC | CCA | CCA | GAG | CGG | GGG | GCT | 3696 |
| Phe | Asp | Asn | Leu | Tyr | Tyr | Trp | Asp | Gln | Asp | Pro | Pro | Glu | Arg | Gly | Ala |      |
|     |     |     |     | 1220|     |     |     |     | 1225|     |     |     |     | 1230|     |      |
| CCA | CCC | AGC | ACC | TTC | AAA | GGG | ACA | CCT | ACG | GCA | GAG | AAC | CCA | GAG | TAC | 3744 |
| Pro | Pro | Ser | Thr | Phe | Lys | Gly | Thr | Pro | Thr | Ala | Glu | Asn | Pro | Glu | Tyr |      |
|     |     |     | 1235|     |     |     |     | 1240|     |     |     |     | 1245|     |     |      |
| CTG | GGT | CTG | GAC | GTG | CCA | GTG | TGA |     |     |     |     |     |     |     |     | 3768 |
| Leu | Gly | Leu | Asp | Val | Pro | Val |     |     |     |     |     |     |     |     |     |      |
|     |     | 1250|     |     |     | 1255|     |     |     |     |     |     |     |     |     |      |

( 2 ) INFORMATION FOR SEQ ID NO:2:

( i ) SEQUENCE CHARACTERISTICS:
        ( A ) LENGTH: 1255 amino acids
        ( B ) TYPE: amino acid (D) TOPOLOGY: linear (ii) MOLECULE TYPE: protein (xi) SEQUENCE DESCRIPTION: SEQ ID NO:2:

| Met | Glu | Leu | Ala | Ala | Leu | Cys | Arg | Trp | Gly | Leu | Leu | Leu | Ala | Leu | Leu |
|---|---|---|---|---|---|---|---|---|---|---|---|---|---|---|---|
| 1 | | | | 5 | | | | | 10 | | | | | 15 | |
| Pro | Pro | Gly | Ala | Ala | Ser | Thr | Gln | Val | Cys | Thr | Gly | Thr | Asp | Met | Lys |
| | | | 20 | | | | 25 | | | | | 30 | | | |
| Leu | Arg | Leu | Pro | Ala | Ser | Pro | Glu | Thr | His | Leu | Asp | Met | Leu | Arg | His |
| | | 35 | | | | | 40 | | | | | 45 | | | |
| Leu | Tyr | Gln | Gly | Cys | Gln | Val | Val | Gln | Gly | Asn | Leu | Glu | Leu | Thr | Tyr |
| | 50 | | | | | 55 | | | | | 60 | | | | |
| Leu | Pro | Thr | Asn | Ala | Ser | Leu | Ser | Phe | Leu | Gln | Asp | Ile | Gln | Glu | Val |
| 65 | | | | | 70 | | | | | 75 | | | | | 80 |
| Gln | Gly | Tyr | Val | Leu | Ile | Ala | His | Asn | Gln | Val | Arg | Gln | Val | Pro | Leu |
| | | | | 85 | | | | | 90 | | | | | 95 | |
| Gln | Arg | Leu | Arg | Ile | Val | Arg | Gly | Thr | Gln | Leu | Phe | Glu | Asp | Asn | Tyr |
| | | | 100 | | | | | 105 | | | | | 110 | | |
| Ala | Leu | Ala | Val | Leu | Asp | Asn | Gly | Asp | Pro | Leu | Asn | Asn | Thr | Thr | Pro |
| | | 115 | | | | | 120 | | | | | 125 | | | |
| Val | Thr | Gly | Ala | Ser | Pro | Gly | Gly | Leu | Arg | Glu | Leu | Gln | Leu | Arg | Ser |
| | 130 | | | | | 135 | | | | | 140 | | | | |
| Leu | Thr | Glu | Ile | Leu | Lys | Gly | Gly | Val | Leu | Ile | Gln | Arg | Asn | Pro | Gln |
| 145 | | | | | 150 | | | | | 155 | | | | | 160 |
| Leu | Cys | Tyr | Gln | Asp | Thr | Ile | Leu | Trp | Lys | Asp | Ile | Phe | His | Lys | Asn |
| | | | | 165 | | | | | 170 | | | | | 175 | |
| Asn | Gln | Leu | Ala | Leu | Thr | Leu | Ile | Asp | Thr | Asn | Arg | Ser | Arg | Ala | Cys |
| | | | 180 | | | | | 185 | | | | | 190 | | |
| His | Pro | Cys | Ser | Pro | Met | Cys | Lys | Gly | Ser | Arg | Cys | Trp | Gly | Glu | Ser |
| | | 195 | | | | | 200 | | | | | 205 | | | |
| Ser | Glu | Asp | Cys | Gln | Ser | Leu | Thr | Arg | Thr | Val | Cys | Ala | Gly | Gly | Cys |
| | 210 | | | | | 215 | | | | | 220 | | | | |
| Ala | Arg | Cys | Lys | Gly | Pro | Leu | Pro | Thr | Asp | Cys | Cys | His | Glu | Gln | Cys |
| 225 | | | | | 230 | | | | | 235 | | | | | 240 |
| Ala | Ala | Gly | Cys | Thr | Gly | Pro | Lys | His | Ser | Asp | Cys | Leu | Ala | Cys | Leu |
| | | | | 245 | | | | | 250 | | | | | 255 | |
| His | Phe | Asn | His | Ser | Gly | Ile | Cys | Glu | Leu | His | Cys | Pro | Ala | Leu | Val |
| | | | 260 | | | | | 265 | | | | | 270 | | |
| Thr | Tyr | Asn | Thr | Asp | Thr | Phe | Glu | Ser | Met | Pro | Asn | Pro | Glu | Gly | Arg |
| | | 275 | | | | | 280 | | | | | 285 | | | |
| Tyr | Thr | Phe | Gly | Ala | Ser | Cys | Val | Thr | Ala | Cys | Pro | Tyr | Asn | Tyr | Leu |
| | 290 | | | | | 295 | | | | | 300 | | | | |
| Ser | Thr | Asp | Val | Gly | Ser | Cys | Thr | Leu | Val | Cys | Pro | Leu | His | Asn | Gln |
| 305 | | | | | 310 | | | | | 315 | | | | | 320 |
| Glu | Val | Thr | Ala | Glu | Asp | Gly | Thr | Gln | Arg | Cys | Glu | Lys | Cys | Ser | Lys |
| | | | | 325 | | | | | 330 | | | | | 335 | |
| Pro | Cys | Ala | Arg | Val | Cys | Tyr | Gly | Leu | Gly | Met | Glu | His | Leu | Arg | Glu |
| | | | 340 | | | | | 345 | | | | | 350 | | |
| Val | Arg | Ala | Val | Thr | Ser | Ala | Asn | Ile | Gln | Glu | Phe | Ala | Gly | Cys | Lys |
| | | 355 | | | | | 360 | | | | | 365 | | | |
| Lys | Ile | Phe | Gly | Ser | Leu | Ala | Phe | Leu | Pro | Glu | Ser | Phe | Asp | Gly | Asp |
| | 370 | | | | | 375 | | | | | 380 | | | | |
| Pro | Ala | Ser | Asn | Thr | Ala | Pro | Leu | Gln | Pro | Glu | Gln | Leu | Gln | Val | Phe |
| 385 | | | | | 390 | | | | | 395 | | | | | 400 |

-continued

```
Glu  Thr  Leu  Glu  Glu  Ile  Thr  Gly  Tyr  Leu  Tyr  Ile  Ser  Ala  Trp  Pro
               405                      410                      415

Asp  Ser  Leu  Pro  Asp  Leu  Ser  Val  Phe  Gln  Asn  Leu  Gln  Val  Ile  Arg
               420                      425                      430

Gly  Arg  Ile  Leu  His  Asn  Gly  Ala  Tyr  Ser  Leu  Thr  Leu  Gln  Gly  Leu
               435                      440                      445

Gly  Ile  Ser  Trp  Leu  Gly  Leu  Arg  Ser  Leu  Arg  Glu  Leu  Gly  Ser  Gly
     450                           455                      460

Leu  Ala  Leu  Ile  His  His  Asn  Thr  His  Leu  Cys  Phe  Val  His  Thr  Val
465                      470                      475                      480

Pro  Trp  Asp  Gln  Leu  Phe  Arg  Asn  Pro  His  Gln  Ala  Leu  Leu  His  Thr
               485                      490                      495

Ala  Asn  Arg  Pro  Glu  Asp  Glu  Cys  Val  Gly  Glu  Gly  Leu  Ala  Cys  His
               500                      505                      510

Gln  Leu  Cys  Ala  Arg  Gly  His  Cys  Trp  Gly  Pro  Gly  Pro  Thr  Gln  Cys
               515                      520                      525

Val  Asn  Cys  Ser  Gln  Phe  Leu  Arg  Gly  Gln  Glu  Cys  Val  Glu  Glu  Cys
          530                      535                      540

Arg  Val  Leu  Gln  Gly  Leu  Pro  Arg  Glu  Tyr  Val  Asn  Ala  Arg  His  Cys
545                           550                      555                      560

Leu  Pro  Cys  His  Pro  Glu  Cys  Gln  Pro  Gln  Asn  Gly  Ser  Val  Thr  Cys
                    565                      570                      575

Phe  Gly  Pro  Glu  Ala  Asp  Gln  Cys  Val  Ala  Cys  Ala  His  Tyr  Lys  Asp
               580                      585                      590

Pro  Pro  Phe  Cys  Val  Ala  Arg  Cys  Pro  Ser  Gly  Val  Lys  Pro  Asp  Leu
               595                      600                      605

Ser  Tyr  Met  Pro  Ile  Trp  Lys  Phe  Pro  Asp  Glu  Glu  Gly  Ala  Cys  Gln
     610                           615                      620

Pro  Cys  Pro  Ile  Asn  Cys  Thr  His  Ser  Cys  Val  Asp  Leu  Asp  Asp  Lys
625                           630                      635                      640

Gly  Cys  Pro  Ala  Glu  Gln  Arg  Ala  Ser  Pro  Leu  Thr  Ser  Ile  Ile  Ser
               645                      650                      655

Ala  Val  Val  Gly  Ile  Leu  Leu  Val  Val  Leu  Gly  Val  Val  Phe  Gly
               660                      665                      670

Ile  Leu  Ile  Lys  Arg  Arg  Gln  Gln  Lys  Ile  Arg  Lys  Tyr  Thr  Met  Arg
          675                      680                      685

Arg  Leu  Leu  Gln  Glu  Thr  Glu  Leu  Val  Glu  Pro  Leu  Thr  Pro  Ser  Gly
     690                      695                      700

Ala  Met  Pro  Asn  Gln  Ala  Gln  Met  Arg  Ile  Leu  Lys  Glu  Thr  Glu  Leu
705                      710                      715                      720

Arg  Lys  Val  Lys  Val  Leu  Gly  Ser  Gly  Ala  Phe  Gly  Thr  Val  Tyr  Lys
                    725                      730                      735

Gly  Ile  Trp  Ile  Pro  Asp  Gly  Glu  Asn  Val  Lys  Ile  Pro  Val  Ala  Ile
               740                      745                      750

Lys  Val  Leu  Arg  Glu  Asn  Thr  Ser  Pro  Lys  Ala  Asn  Lys  Glu  Ile  Leu
          755                      760                      765

Asp  Glu  Ala  Tyr  Val  Met  Ala  Gly  Val  Gly  Ser  Pro  Tyr  Val  Ser  Arg
     770                      775                      780

Leu  Leu  Gly  Ile  Cys  Leu  Thr  Ser  Thr  Val  Gln  Leu  Val  Thr  Gln  Leu
785                      790                      795                      800

Met  Pro  Tyr  Gly  Cys  Leu  Leu  Asp  His  Val  Arg  Glu  Asn  Arg  Gly  Arg
               805                      810                      815

Leu  Gly  Ser  Gln  Asp  Leu  Leu  Asn  Trp  Cys  Met  Gln  Ile  Ala  Lys  Gly
```

```
                        820                           825                           830
Met  Ser  Tyr  Leu  Glu  Asp  Val  Arg  Leu  Val  His  Arg  Asp  Leu  Ala  Ala
               835                           840                      845

Arg  Asn  Val  Leu  Val  Lys  Ser  Pro  Asn  His  Val  Lys  Ile  Thr  Asp  Phe
     850                      855                           860

Gly  Leu  Ala  Arg  Leu  Leu  Asp  Ile  Asp  Glu  Thr  Glu  Tyr  His  Ala  Asp
865                           870                      875                      880

Gly  Gly  Lys  Val  Pro  Ile  Lys  Trp  Met  Ala  Leu  Glu  Ser  Ile  Leu  Arg
                    885                      890                           895

Arg  Arg  Phe  Thr  His  Gln  Ser  Asp  Val  Trp  Ser  Tyr  Gly  Val  Thr  Val
                    900                           905                      910

Trp  Glu  Leu  Met  Thr  Phe  Gly  Ala  Lys  Pro  Tyr  Asp  Gly  Ile  Pro  Ala
               915                           920                 925

Arg  Glu  Ile  Pro  Asp  Leu  Leu  Glu  Lys  Gly  Glu  Arg  Leu  Pro  Gln  Pro
               930                      935                      940

Pro  Ile  Cys  Thr  Ile  Asp  Val  Tyr  Met  Ile  Met  Val  Lys  Cys  Trp  Met
945                           950                      955                      960

Ile  Asp  Ser  Glu  Cys  Arg  Pro  Arg  Phe  Arg  Glu  Leu  Val  Ser  Glu  Phe
                    965                      970                      975

Ser  Arg  Met  Ala  Arg  Asp  Pro  Gln  Arg  Phe  Val  Val  Ile  Gln  Asn  Glu
               980                      985                           990

Asp  Leu  Gly  Pro  Ala  Ser  Pro  Leu  Asp  Ser  Thr  Phe  Tyr  Arg  Ser  Leu
          995                      1000                     1005

Leu  Glu  Asp  Asp  Asp  Met  Gly  Asp  Leu  Val  Asp  Ala  Glu  Glu  Tyr  Leu
          1010                          1015                     1020

Val  Pro  Gln  Gln  Gly  Phe  Phe  Cys  Pro  Asp  Pro  Ala  Pro  Gly  Ala  Gly
1025                          1030                     1035                     1040

Gly  Met  Val  His  His  Arg  His  Arg  Ser  Ser  Ser  Thr  Arg  Ser  Gly  Gly
                    1045                          1050                     1055

Gly  Asp  Leu  Thr  Leu  Gly  Leu  Glu  Pro  Ser  Glu  Glu  Glu  Ala  Pro  Arg
               1060                     1065                          1070

Ser  Pro  Leu  Ala  Pro  Ser  Glu  Gly  Ala  Gly  Ser  Asp  Val  Phe  Asp  Gly
          1075                     1080                          1085

Asp  Leu  Gly  Met  Gly  Ala  Ala  Lys  Gly  Leu  Gln  Ser  Leu  Pro  Thr  His
     1090                          1095                     1100

Asp  Pro  Ser  Pro  Leu  Gln  Arg  Tyr  Ser  Glu  Asp  Pro  Thr  Val  Pro  Leu
1105                     1110                          1115                     1120

Pro  Ser  Glu  Thr  Asp  Gly  Tyr  Val  Ala  Pro  Leu  Thr  Cys  Ser  Pro  Gln
                    1125                          1130                     1135

Pro  Glu  Tyr  Val  Asn  Gln  Pro  Asp  Val  Arg  Pro  Gln  Pro  Pro  Ser  Pro
               1140                          1145                     1150

Arg  Glu  Gly  Pro  Leu  Pro  Ala  Ala  Arg  Pro  Ala  Gly  Ala  Thr  Leu  Glu
          1155                          1160                     1165

Arg  Pro  Lys  Thr  Leu  Ser  Pro  Gly  Lys  Asn  Gly  Val  Val  Lys  Asp  Val
          1170                     1175                          1180

Phe  Ala  Phe  Gly  Gly  Ala  Val  Glu  Asn  Pro  Glu  Tyr  Leu  Thr  Pro  Gln
1185                          1190                     1195                     1200

Gly  Gly  Ala  Ala  Pro  Gln  Pro  His  Pro  Pro  Ala  Phe  Ser  Pro  Ala
                    1205                     1210                     1215

Phe  Asp  Asn  Leu  Tyr  Tyr  Trp  Asp  Gln  Asp  Pro  Pro  Glu  Arg  Gly  Ala
               1220                     1225                          1230

Pro  Pro  Ser  Thr  Phe  Lys  Gly  Thr  Pro  Thr  Ala  Glu  Asn  Pro  Glu  Tyr
          1235                     1240                          1245
```

```
Leu Gly Leu Asp Val Pro Val
    1250                1255
```

( 2 ) INFORMATION FOR SEQ ID NO:3:

( i ) SEQUENCE CHARACTERISTICS:
        ( A ) LENGTH: 732 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..732
        ( D ) OTHER INFORMATION: /note= "product = "520C9sFv protein"

( x i ) SEQUENCE DESCRIPTION: SEQ ID NO:3:

```
GAG ATC CAA TTG GTG CAG TCT GGA CCT GAG CTG AAG AAG CCT GGA GAG    48
Glu Ile Gln Leu Val Gln Ser Gly Pro Glu Leu Lys Lys Pro Gly Glu
 1               5                  10                  15

ACA GTC AAG ATC TCC TGC AAG GCT TCT GGA TAT ACC TTC GCA AAC TAT    96
Thr Val Lys Ile Ser Cys Lys Ala Ser Gly Tyr Thr Phe Ala Asn Tyr
             20                  25                  30

GGA ATG AAC TGG ATG AAG CAG GCT CCA GGA AAG GGT TTA AAG TGG ATG   144
Gly Met Asn Trp Met Lys Gln Ala Pro Gly Lys Gly Leu Lys Trp Met
         35                  40                  45

GGC TGG ATA AAC ACC TAC ACT GGA CAG TCA ACA TAT GCT GAT GAC TTC   192
Gly Trp Ile Asn Thr Tyr Thr Gly Gln Ser Thr Tyr Ala Asp Asp Phe
     50                  55                  60

AAG GAA CGG TTT GCC TTC TCT TTG GAA ACC TCT GCC ACC ACT GCC CAT   240
Lys Glu Arg Phe Ala Phe Ser Leu Glu Thr Ser Ala Thr Thr Ala His
 65                  70                  75                  80

TTG CAG ATC AAC AAC CTC AGA AAT GAG GAC TCG GCC ACA TAT TTC TGT   288
Leu Gln Ile Asn Asn Leu Arg Asn Glu Asp Ser Ala Thr Tyr Phe Cys
                 85                  90                  95

GCA AGA CGA TTT GGG TTT GCT TAC TGG GGC CAA GGG ACT CTG GTC AGT   336
Ala Arg Arg Phe Gly Phe Ala Tyr Trp Gly Gln Gly Thr Leu Val Ser
            100                 105                 110

GTC TCT GCA TCG ATA TCG AGC TCC TCC GGA TCT TCA TCT AGC GGT TCC   384
Val Ser Ala Ser Ile Ser Ser Ser Ser Gly Ser Ser Ser Ser Gly Ser
        115                 120                 125

AGC TCG AGT GGA TCC GAT ATC CAG ATG ACC CAG TCT CCA TCC TCC TTA   432
Ser Ser Ser Gly Ser Asp Ile Gln Met Thr Gln Ser Pro Ser Ser Leu
130                 135                 140

TCT GCC TCT CTG GGA GAA AGA GTC AGT CTC ACT TGT CGG GCA AGT CAG   480
Ser Ala Ser Leu Gly Glu Arg Val Ser Leu Thr Cys Arg Ala Ser Gln
145                 150                 155                 160

GAC ATT GGT AAT AGC TTA ACC TGG CTT CAG CAG GAA CCA GAT GGA ACT   528
Asp Ile Gly Asn Ser Leu Thr Trp Leu Gln Gln Glu Pro Asp Gly Thr
                165                 170                 175

ATT AAA CGC CTG ATC TAC GCC ACA TCC AGT TTA GAT TCT GGT GTC CCC   576
Ile Lys Arg Leu Ile Tyr Ala Thr Ser Ser Leu Asp Ser Gly Val Pro
            180                 185                 190

AAA AGG TTC AGT GGC AGT CGG TCT GGG TCA GAT TAT TCT CTC ACC ATC   624
Lys Arg Phe Ser Gly Ser Arg Ser Gly Ser Asp Tyr Ser Leu Thr Ile
        195                 200                 205

AGT AGC CTT GAG TCT GAA GAT TTT GTA GTC TAT TAC TGT CTA CAA TAT   672
Ser Ser Leu Glu Ser Glu Asp Phe Val Val Tyr Tyr Cys Leu Gln Tyr
210                 215                 220

GCT ATT TTT CCG TAC ACG TTC GGA GGG GGG ACC AAC CTG GAA ATA AAA   720
Ala Ile Phe Pro Tyr Thr Phe Gly Gly Gly Thr Asn Leu Glu Ile Lys
225                 230                 235                 240
```

```
CGG GCT GAT TAA                                                                                          732
Arg Ala Asp
```

( 2 ) INFORMATION FOR SEQ ID NO:4:

( i ) SEQUENCE CHARACTERISTICS:
    ( A ) LENGTH: 243 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

```
Glu Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Ala Asn Tyr
             20                  25                  30

Gly Met Asn Trp Met Lys Gln Ala Pro Gly Lys Gly Leu Lys Trp Met
         35                  40                  45

Gly Trp Ile Asn Thr Tyr Thr Gly Gln Ser Thr Tyr Ala Asp Asp Phe
     50                  55                  60

Lys Glu Arg Phe Ala Phe Ser Leu Glu Thr Ser Ala Thr Thr Ala His
 65              70                  75                      80

Leu Gln Ile Asn Asn Leu Arg Asn Glu Asp Ser Ala Thr Tyr Phe Cys
                 85                  90                      95

Ala Arg Arg Phe Gly Phe Ala Tyr Trp Gly Gln Gly Thr Leu Val Ser
             100                 105                 110

Val Ser Ala Ser Ile Ser Ser Ser Ser Gly Ser Ser Ser Ser Gly Ser
             115                 120                 125

Ser Ser Ser Gly Ser Asp Ile Gln Met Thr Gln Ser Pro Ser Ser Leu
    130                 135                 140

Ser Ala Ser Leu Gly Glu Arg Val Ser Leu Thr Cys Arg Ala Ser Gln
145                 150                 155                 160

Asp Ile Gly Asn Ser Leu Thr Trp Leu Gln Gln Glu Pro Asp Gly Thr
             165                 170                 175

Ile Lys Arg Leu Ile Tyr Ala Thr Ser Ser Leu Asp Ser Gly Val Pro
             180                 185                 190

Lys Arg Phe Ser Gly Ser Arg Ser Gly Ser Asp Tyr Ser Leu Thr Ile
         195                 200                 205

Ser Ser Leu Glu Ser Glu Asp Phe Val Val Tyr Tyr Cys Leu Gln Tyr
    210                 215                 220

Ala Ile Phe Pro Tyr Thr Phe Gly Gly Gly Thr Asn Leu Glu Ile Lys
225                 230                 235                 240

Arg Ala Asp
```

( 2 ) INFORMATION FOR SEQ ID NO:5: DELETED ACCORDING TO:
              PRELIMINARY AMENDMENT ( 2 ) INFORMATION FOR SEQ ID NO:6: DELETED ACCORDING TO:
              PRELIMINARY AMENDMENT ( 2 ) INFORMATION FOR SEQ ID NO:7:

( i ) SEQUENCE CHARACTERISTICS:
    ( A ) LENGTH: 807 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 1..807
    ( D ) OTHER INFORMATION: /note= "product = "Ricin-A chain"

( x i ) SEQUENCE DESCRIPTION: SEQ ID NO:7:

| ATG | ATA | TTC | CCC | AAA | CAA | TA (i) SEQUENCE CHARACTERISTICS:
  (A) LENGTH: 268 amino acids
  (B) TYPE: amino acid
  (D) TOPOLOGY: linear (ii) MOLECULE TYPE: protein (xi) SEQUENCE DESCRIPTION: SEQ ID NO:8:

| Met | Ile | Phe | Pro | Lys | Gln | Tyr | Pro | Ile | Ile | Asn | Phe | Thr | Thr | Ala | Gly |
|---|---|---|---|---|---|---|---|---|---|---|---|---|---|---|---|
| 1 | | | | 5 | | | | | 10 | | | | | 15 | |

| Ala | Thr | Val | Gln | Ser | Tyr | Thr | Asn | Phe | Ile | Arg | Ala | Val | Arg | Gly | Arg |
|---|---|---|---|---|---|---|---|---|---|---|---|---|---|---|---|
| | | | 20 | | | | | 25 | | | | | 30 | | |

| Leu | Thr | Thr | Gly | Ala | Asp | Val | Arg | His | Glu | Ile | Pro | Val | Leu | Pro | Asn |
|---|---|---|---|---|---|---|---|---|---|---|---|---|---|---|---|
| | | 35 | | | | | 40 | | | | | 45 | | | |

| Arg | Val | Gly | Leu | Pro | Ile | Asn | Gln | Arg | Phe | Ile | Leu | Val | Glu | Leu | Ser |
|---|---|---|---|---|---|---|---|---|---|---|---|---|---|---|---|
| | 50 | | | | | 55 | | | | | 60 | | | | |

| Asn | His | Ala | Glu | Leu | Ser | Val | Thr | Leu | Ala | Leu | Asp | Val | Thr | Asn | Ala |
|---|---|---|---|---|---|---|---|---|---|---|---|---|---|---|---|
| 65 | | | | | 70 | | | | | 75 | | | | | 80 |

| Tyr | Val | Val | Gly | Tyr | Arg | Ala | Gly | Asn | Ser | Ala | Tyr | Phe | Phe | His | Pro |
|---|---|---|---|---|---|---|---|---|---|---|---|---|---|---|---|
| | | | | 85 | | | | | 90 | | | | | 95 | |

| Asp | Asn | Gln | Glu | Asp | Ala | Glu | Ala | Ile | Thr | His | Leu | Phe | Thr | Asp | Val |
|---|---|---|---|---|---|---|---|---|---|---|---|---|---|---|---|
| | | | 100 | | | | | 105 | | | | | 110 | | |

| Gln | Asn | Arg | Tyr | Thr | Phe | Ala | Phe | Gly | Gly | Asn | Tyr | Asp | Arg | Leu | Glu |
|---|---|---|---|---|---|---|---|---|---|---|---|---|---|---|---|
| | | 115 | | | | | 120 | | | | | 125 | | | |

| Gln | Leu | Ala | Gly | Asn | Leu | Arg | Glu | Asn | Ile | Glu | Leu | Gly | Asn | Gly | Pro |
|---|---|---|---|---|---|---|---|---|---|---|---|---|---|---|---|
| | 130 | | | | | 135 | | | | | 140 | | | | |

| Leu | Glu | Glu | Ala | Ile | Ser | Ala | Leu | Tyr | Tyr | Tyr | Ser | Thr | Gly | Gly | Thr |
|---|---|---|---|---|---|---|---|---|---|---|---|---|---|---|---|
| 145 | | | | | 150 | | | | | 155 | | | | | 160 |

| Gln | Leu | Pro | Thr | Leu | Ala | Arg | Ser | Phe | Ile | Ile | Cys | Ile | Gln | Met | Ile |
|---|---|---|---|---|---|---|---|---|---|---|---|---|---|---|---|
| | | | | 165 | | | | | 170 | | | | | 175 | |

| Ser | Glu | Ala | Ala | Arg | Phe | Gln | Tyr | Ile | Glu | Gly | Glu | Met | Arg | Thr | Arg |
|---|---|---|---|---|---|---|---|---|---|---|---|---|---|---|---|
| | | | | 180 | | | | | 185 | | | | | 190 | |

| Ile | Arg | Tyr | Asn | Arg | Arg | Ser | Ala | Pro | Asp | Pro | Ser | Val | Ile | Thr | Leu |
|---|---|---|---|---|---|---|---|---|---|---|---|---|---|---|---|
| | | | 195 | | | | | 200 | | | | | 205 | | |

| Glu | Asn | Ser | Trp | Gly | Arg | Leu | Ser | Thr | Ala | Ile | Gln | Glu | Ser | Asn | Gln |
|---|---|---|---|---|---|---|---|---|---|---|---|---|---|---|---|
| | 210 | | | | | 215 | | | | | 220 | | | | |

| Gly | Ala | Phe | Ala | Ser | Pro | Ile | Gln | Leu | Gln | Arg | Arg | Asn | Gly | Ser | Lys |
|---|---|---|---|---|---|---|---|---|---|---|---|---|---|---|---|
| 225 | | | | | 230 | | | | | 235 | | | | | 240 |

| Phe | Ser | Val | Tyr | Asp | Val | Ser | Ile | Leu | Ile | Pro | Ile | Ile | Ala | Leu | Met |
|---|---|---|---|---|---|---|---|---|---|---|---|---|---|---|---|
| | | | | 245 | | | | | 250 | | | | | 255 | |

| Val | Tyr | Arg | Cys | Ala | Pro | Pro | Pro | Ser | Ser | Gln | Phe |
|---|---|---|---|---|---|---|---|---|---|---|---|
| | | | 260 | | | | | 265 | | | |

(2) INFORMATION FOR SEQ ID NO:9:

(i) SEQUENCE CHARACTERISTICS:
    (A) LENGTH: 1605 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: CDS
    (B) LOCATION: 1..1605
    (D) OTHER INFORMATION: /note= "product = "G-FIT""

(xi) SEQUENCE DESCRIPTION: SEQ ID NO:9:

| AAG | CTT | ATG | ATA | TTC | CCC | AAA | CAA | TAC | CCA | ATT | ATA | AAC | TTT | ACC | ACA | 48 |
|---|---|---|---|---|---|---|---|---|---|---|---|---|---|---|---|---|
| Lys | Leu | Met | Ile | Phe | Pro | Lys | Gln | Tyr | Pro | Ile | Ile | Asn | Phe | Thr | Thr | |

```
          1                    5                          10                          15
GCG  GGT  GCC  ACT  GTG  CAA  AGC  TAC  ACA  AAC  TTT  ATC  AGA  GCT  GTT  CGC            96
Ala  Gly  Ala  Thr  Val  Gln  Ser  Tyr  Thr  Asn  Phe  Ile  Arg  Ala  Val  Arg
                    20                   25                        30

GGT  CGT  TTA  ACA  ACT  GGA  GCT  GAT  GTG  AGA  CAT  GAA  ATA  CCA  GTG  TTG           144
Gly  Arg  Leu  Thr  Thr  Gly  Ala  Asp  Val  Arg  His  Glu  Ile  Pro  Val  Leu
          35                        40                        45

CCA  AAC  AGA  GTT  GGT  TTG  CCT  ATA  AAC  CAA  CGG  TTT  ATT  TTA  GTT  GAA           192
Pro  Asn  Arg  Val  Gly  Leu  Pro  Ile  Asn  Gln  Arg  Phe  Ile  Leu  Val  Glu
     50                        55                        60

CTC  TCA  AAT  CAT  GCA  GAG  CTT  TCT  GTT  ACA  TTA  GCG  CTG  GAT  GTC  ACC           240
Leu  Ser  Asn  His  Ala  Glu  Leu  Ser  Val  Thr  Leu  Ala  Leu  Asp  Val  Thr
65                        70                        75                        80

AAT  GCA  TAT  GTG  GTA  GGC  TAC  CGT  GCT  GGA  AAT  AGC  GCA  TAT  TTC  TTT           288
Asn  Ala  Tyr  Val  Val  Gly  Tyr  Arg  Ala  Gly  Asn  Ser  Ala  Tyr  Phe  Phe
                    85                        90                        95

CAT  CCT  GAC  AAT  CAG  GAA  GAT  GCA  GAA  GCA  ATC  ACT  CAT  CTT  TTC  ACT           336
His  Pro  Asp  Asn  Gln  Glu  Asp  Ala  Glu  Ala  Ile  Thr  His  Leu  Phe  Thr
                         100                      105                      110

GAT  GTT  CAA  AAT  CGA  TAT  ACA  TTC  GCC  TTT  GGT  GGT  AAT  TAT  GAT  AGA           384
Asp  Val  Gln  Asn  Arg  Tyr  Thr  Phe  Ala  Phe  Gly  Gly  Asn  Tyr  Asp  Arg
                    115                      120                      125

CTT  GAA  CAA  CTT  GCT  GGT  AAT  CTG  AGA  GAA  AAT  ATC  GAG  TTG  GGA  AAT           432
Leu  Glu  Gln  Leu  Ala  Gly  Asn  Leu  Arg  Glu  Asn  Ile  Glu  Leu  Gly  Asn
130                      135                      140

GGT  CCA  CTA  GAG  GAG  GCT  ATC  TCA  GCG  CTT  TAT  TAT  TAC  AGT  ACT  GGT           480
Gly  Pro  Leu  Glu  Glu  Ala  Ile  Ser  Ala  Leu  Tyr  Tyr  Tyr  Ser  Thr  Gly
145                      150                      155                      160

GGC  ACT  CAG  CTT  CCA  ACT  CTG  GCT  CGT  TCC  TTT  ATA  ATT  TGC  ATC  CAA           528
Gly  Thr  Gln  Leu  Pro  Thr  Leu  Ala  Arg  Ser  Phe  Ile  Ile  Cys  Ile  Gln
                    165                      170                      175

ATG  ATT  TCA  GAA  GCA  GCA  AGA  TTC  CAA  TAT  ATT  GAG  GGA  GAA  ATG  CGC           576
Met  Ile  Ser  Glu  Ala  Ala  Arg  Phe  Gln  Tyr  Ile  Glu  Gly  Glu  Met  Arg
               180                      185                      190

ACG  AGA  ATT  AGG  TAC  AAC  CGG  AGA  TCT  GCA  CCA  GAT  CCT  AGC  GTA  ATT           624
Thr  Arg  Ile  Arg  Tyr  Asn  Arg  Arg  Ser  Ala  Pro  Asp  Pro  Ser  Val  Ile
          195                      200                      205

ACA  CTT  GAG  AAT  AGT  TGG  GGG  AGA  CTT  TCC  ACT  GCA  ATT  CAA  GAG  TCT           672
Thr  Leu  Glu  Asn  Ser  Trp  Gly  Arg  Leu  Ser  Thr  Ala  Ile  Gln  Glu  Ser
210                      215                      220

AAC  CAA  GGA  GCC  TTT  GCT  AGT  CCA  ATT  CAA  CTG  CAA  AGA  CGT  AAT  GGT           720
Asn  Gln  Gly  Ala  Phe  Ala  Ser  Pro  Ile  Gln  Leu  Gln  Arg  Arg  Asn  Gly
225                      230                      235                      240

TCC  AAA  TTC  AGT  GTG  TAC  GAT  GTG  AGT  ATA  TTA  ATC  CCT  ATC  ATA  GCT           768
Ser  Lys  Phe  Ser  Val  Tyr  Asp  Val  Ser  Ile  Leu  Ile  Pro  Ile  Ile  Ala
                    245                      250                      255

CTC  ATG  GTG  TAT  AGA  TGC  GCA  CCT  CCA  CCA  TCG  TCA  CAG  TTT  TCT  CTT           816
Leu  Met  Val  Tyr  Arg  Cys  Ala  Pro  Pro  Pro  Ser  Ser  Gln  Phe  Ser  Leu
               260                      265                      270

CTT  ATA  AGG  CCA  GTG  GTA  CCA  AAT  TTT  AAT  GCT  GAT  GTT  TGT  ATG  GAT           864
Leu  Ile  Arg  Pro  Val  Val  Pro  Asn  Phe  Asn  Ala  Asp  Val  Cys  Met  Asp
          275                      280                      285

CCT  GAG  ATC  CAA  TTG  GTG  CAG  TCT  GGA  CCT  GAG  CTG  AAG  AAG  CCT  GGA           912
Pro  Glu  Ile  Gln  Leu  Val  Gln  Ser  Gly  Pro  Glu  Leu  Lys  Lys  Pro  Gly
290                      295                      300

GAG  ACA  GTC  AAG  ATC  TCC  TGC  AAG  GCT  TCT  GGA  TAT  ACC  TTC  GCA  AAC           960
Glu  Thr  Val  Lys  Ile  Ser  Cys  Lys  Ala  Ser  Gly  Tyr  Thr  Phe  Ala  Asn
305                      310                      315                      320

TAT  GGA  ATG  AAC  TGG  ATG  AAG  CAG  GCT  CCA  GGA  AAG  GGT  TTA  AAG  TGG          1008
Tyr  Gly  Met  Asn  Trp  Met  Lys  Gln  Ala  Pro  Gly  Lys  Gly  Leu  Lys  Trp
```

|     |     |     |     |     |     |     |     | 325 |     |     |     |     | 330 |     |     |     |     | 335 |     |      |
|-----|-----|-----|-----|-----|-----|-----|-----|-----|-----|-----|-----|-----|-----|-----|-----|-----|-----|-----|-----|------|

```
ATG  GGC  TGG  ATA  AAC  ACC  TAC  ACT  GGA  CAG  TCA  ACA  TAT  GCT  GAT  GAC      1056
Met  Gly  Trp  Ile  Asn  Thr  Tyr  Thr  Gly  Gln  Ser  Thr  Tyr  Ala  Asp  Asp
               340                      345                 350

TTC  AAG  GAA  CGG  TTT  GCC  TTC  TCT  TTG  GAA  ACC  TCT  GCC  ACC  ACT  GCC      1104
Phe  Lys  Glu  Arg  Phe  Ala  Phe  Ser  Leu  Glu  Thr  Ser  Ala  Thr  Thr  Ala
               355                      360                 365

CAT  TTG  CAG  ATC  AAC  AAC  CTC  AGA  AAT  GAG  GAC  TCG  GCC  ACA  TAT  TTC      1152
His  Leu  Gln  Ile  Asn  Asn  Leu  Arg  Asn  Glu  Asp  Ser  Ala  Thr  Tyr  Phe
          370                      375                 380

TGT  GCA  AGA  CGA  TTT  GGG  TTT  GCT  TAC  TGG  GGC  CAA  GGG  ACT  CTG  GTC      1200
Cys  Ala  Arg  Arg  Phe  Gly  Phe  Ala  Tyr  Trp  Gly  Gln  Gly  Thr  Leu  Val
385                           390                 395                      400

AGT  GTC  TCT  GCA  TCG  ATA  TCG  AGC  TCT  GGT  GGC  GGT  GGC  TCG  GGC  GGT      1248
Ser  Val  Ser  Ala  Ser  Ile  Ser  Ser  Ser  Gly  Gly  Gly  Gly  Ser  Gly  Gly
                         405                      410                 415

GGT  GGG  TCG  GGT  GGC  GGC  GGA  TCG  GAT  ATC  CAG  ATG  ACC  CAG  TCT  CCA      1296
Gly  Gly  Ser  Gly  Gly  Gly  Gly  Ser  Asp  Ile  Gln  Met  Thr  Gln  Ser  Pro
               420                      425                 430

TCC  TCC  TTA  TCT  GCC  TCT  CTG  GGA  GAA  AGA  GTC  AGT  CTC  ACT  TGT  CGG      1344
Ser  Ser  Leu  Ser  Ala  Ser  Leu  Gly  Glu  Arg  Val  Ser  Leu  Thr  Cys  Arg
          435                      440                 445

GCA  AGT  CAG  GAC  ATT  GGT  AAT  AGC  TTA  ACC  TGG  CTT  TCA  CAG  GAA  CCA      1392
Ala  Ser  Gln  Asp  Ile  Gly  Asn  Ser  Leu  Thr  Trp  Leu  Ser  Gln  Glu  Pro
     450                      455                 460

GAT  GGA  ACT  ATT  AAA  CGC  CTG  ATC  TAC  GCC  ACA  TCC  AGT  TTA  GAT  TCT      1440
Asp  Gly  Thr  Ile  Lys  Arg  Leu  Ile  Tyr  Ala  Thr  Ser  Ser  Leu  Asp  Ser
465                      470                 475                      480

GGT  GTC  CCC  AAA  AGG  TTC  AGT  GGC  AGT  CGG  TCT  GGG  TCA  GAT  TAT  TCT      1488
Gly  Val  Pro  Lys  Arg  Phe  Ser  Gly  Ser  Arg  Ser  Gly  Ser  Asp  Tyr  Ser
                    485                      490                 495

CTC  ACC  ATC  AGT  AGC  CTT  GAG  TCT  GAA  GAT  TTT  GTA  GTC  TAT  TAC  TGT      1536
Leu  Thr  Ile  Ser  Ser  Leu  Glu  Ser  Glu  Asp  Phe  Val  Val  Tyr  Tyr  Cys
               500                      505                 510

CTA  CAA  TAT  GCT  ATT  TTT  CCG  TAC  ACG  TTC  GGA  GGG  GGG  ACC  AAC  CTG      1584
Leu  Gln  Tyr  Ala  Ile  Phe  Pro  Tyr  Thr  Phe  Gly  Gly  Gly  Thr  Asn  Leu
          515                      520                 525

GAA  ATA  AAA  CGG  GCT  GAT  TAA                                                    1605
Glu  Ile  Lys  Arg  Ala  Asp
530
```

( 2 ) INFORMATION FOR SEQ ID NO:10:

( i ) SEQUENCE CHARACTERISTICS:
        ( A ) LENGTH: 534 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Lys  Leu  Met  Ile  Phe  Pro  Lys  Gln  Tyr  Pro  Ile  Ile  Asn  Phe  Thr  Thr
1                   5                        10                      15

Ala  Gly  Ala  Thr  Val  Gln  Ser  Tyr  Thr  Asn  Phe  Ile  Arg  Ala  Val  Arg
               20                       25                      30

Gly  Arg  Leu  Thr  Thr  Gly  Ala  Asp  Val  Arg  His  Glu  Ile  Pro  Val  Leu
          35                       40                      45

Pro  Asn  Arg  Val  Gly  Leu  Pro  Ile  Asn  Gln  Arg  Phe  Ile  Leu  Val  Glu
     50                       55                      60

Leu  Ser  Asn  His  Ala  Glu  Leu  Ser  Val  Thr  Leu  Ala  Leu  Asp  Val  Thr
65                       70                      75                       80
```

```
Asn Ala Tyr Val Val Gly Tyr Arg Ala Gly Asn Ser Ala Tyr Phe Phe
                85                  90                  95
His Pro Asp Asn Gln Glu Asp Ala Glu Ala Ile Thr His Leu Phe Thr
            100                 105                 110
Asp Val Gln Asn Arg Tyr Thr Phe Ala Phe Gly Gly Asn Tyr Asp Arg
        115                 120                 125
Leu Glu Gln Leu Ala Gly Asn Leu Arg Glu Asn Ile Glu Leu Gly Asn
    130                 135                 140
Gly Pro Leu Glu Glu Ala Ile Ser Ala Leu Tyr Tyr Ser Thr Gly
145                 150                 155                 160
Gly Thr Gln Leu Pro Thr Leu Ala Arg Ser Phe Ile Ile Cys Ile Gln
                165                 170                 175
Met Ile Ser Glu Ala Ala Arg Phe Gln Tyr Ile Glu Gly Glu Met Arg
            180                 185                 190
Thr Arg Ile Arg Tyr Asn Arg Arg Ser Ala Pro Asp Pro Ser Val Ile
        195                 200                 205
Thr Leu Glu Asn Ser Trp Gly Arg Leu Ser Thr Ala Ile Gln Glu Ser
    210                 215                 220
Asn Gln Gly Ala Phe Ala Ser Pro Ile Gln Leu Gln Arg Arg Asn Gly
225                 230                 235                 240
Ser Lys Phe Ser Val Tyr Asp Val Ser Ile Leu Ile Pro Ile Ile Ala
                245                 250                 255
Leu Met Val Tyr Arg Cys Ala Pro Pro Ser Ser Gln Phe Ser Leu
            260                 265                 270
Leu Ile Arg Pro Val Val Pro Asn Phe Asn Ala Asp Val Cys Met Asp
        275                 280                 285
Pro Glu Ile Gln Leu Val Gln Ser Gly Pro Glu Leu Lys Lys Pro Gly
    290                 295                 300
Glu Thr Val Lys Ile Ser Cys Lys Ala Ser Gly Tyr Thr Phe Ala Asn
305                 310                 315                 320
Tyr Gly Met Asn Trp Met Lys Gln Ala Pro Gly Lys Gly Leu Lys Trp
                325                 330                 335
Met Gly Trp Ile Asn Thr Tyr Thr Gly Gln Ser Thr Tyr Ala Asp Asp
            340                 345                 350
Phe Lys Glu Arg Phe Ala Phe Ser Leu Glu Thr Ser Ala Thr Thr Ala
        355                 360                 365
His Leu Gln Ile Asn Asn Leu Arg Asn Glu Asp Ser Ala Thr Tyr Phe
    370                 375                 380
Cys Ala Arg Arg Phe Gly Phe Ala Tyr Trp Gly Gln Gly Thr Leu Val
385                 390                 395                 400
Ser Val Ser Ala Ser Ile Ser Ser Ser Gly Gly Gly Gly Ser Gly Gly
                405                 410                 415
Gly Gly Ser Gly Gly Gly Gly Ser Asp Ile Gln Met Thr Gln Ser Pro
            420                 425                 430
Ser Ser Leu Ser Ala Ser Leu Gly Glu Arg Val Ser Leu Thr Cys Arg
        435                 440                 445
Ala Ser Gln Asp Ile Gly Asn Ser Leu Thr Trp Leu Ser Gln Glu Pro
    450                 455                 460
Asp Gly Thr Ile Lys Arg Leu Ile Tyr Ala Thr Ser Ser Leu Asp Ser
465                 470                 475                 480
Gly Val Pro Lys Arg Phe Ser Gly Ser Arg Ser Gly Ser Asp Tyr Ser
                485                 490                 495
Leu Thr Ile Ser Ser Leu Glu Ser Glu Asp Phe Val Val Tyr Tyr Cys
```

Leu Gln Tyr Ala Ile Phe Pro Tyr Thr Phe Gly Gly Gly Thr Asn Leu
    515                 520                 525

Glu Ile Lys Arg Ala Asp
    530

(2) INFORMATION FOR SEQ ID NO:11:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..45
        (D) OTHER INFORMATION: /note= "product = "new linker/
            info: new linker""

(xi) SEQUENCE DESCRIPTION: SEQ ID NO:11:

TCG AGC TCC TCC GGA TCT TCA TCT AGC GGT TCC AGC TCG AGT GGA    45
Ser Ser Ser Ser Gly Ser Ser Ser Ser Gly Ser Ser Ser Ser Gly
 1               5                  10                  15

(2) INFORMATION FOR SEQ ID NO:12:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:12:

Ser Ser Ser Ser Gly Ser Ser Ser Ser Gly Ser Ser Ser Ser Gly
 1               5                  10                  15

(2) INFORMATION FOR SEQ ID NO:13:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..45
        (D) OTHER INFORMATION: /note= "product = "old linker/
            protein info: old linker""

(xi) SEQUENCE DESCRIPTION: SEQ ID NO:13:

GGA GGA GGA GGA TCT GGA GGA GGA GGA TCT GGA GGA GGA GGA TCT    45
Gly Gly Gly Gly Ser Gly Gly Gly Gly Ser Gly Gly Gly Gly Ser
 1               5                  10                  15

(2) INFORMATION FOR SEQ ID NO:14:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:14:

```
Gly Gly Gly Gly Ser Gly Gly Gly Gly Ser Gly Gly Gly Gly Ser
 1               5                   10                  15
```

( 2 ) INFORMATION FOR SEQ ID NO:15:

( i ) SEQUENCE CHARACTERISTICS:
        ( A ) LENGTH: 1869 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1869
        ( D ) OTHER INFORMATION: /note= "product = "741sFv-PE40""

( x i ) SEQUENCE DESCRIPTION: SEQ ID NO:15:

```
GAT  CCT  GAG  ATC  CAA  TTG  GTG  CAG  TCT  GGA  CCT  GAG  CTG  AAG  AAG  CCT      48
Asp  Pro  Glu  Ile  Gln  Leu  Val  Gln  Ser  Gly  Pro  Glu  Leu  Lys  Lys  Pro
 1                   5                        10                      15

GGA  GAG  ACA  GTC  AAG  ATC  TCC  TGC  AAG  GCT  TCT  GGG  TAT  ACC  TTC  ACA      96
Gly  Glu  Thr  Val  Lys  Ile  Ser  Cys  Lys  Ala  Ser  Gly  Tyr  Thr  Phe  Thr
          20                        25                       30

AAC  TAT  GGA  ATG  AAC  TGG  GTG  AAG  CAG  GCT  CCA  GGA  AAG  GGT  TTA  AAG     144
Asn  Tyr  Gly  Met  Asn  Trp  Val  Lys  Gln  Ala  Pro  Gly  Lys  Gly  Leu  Lys
               35                        40                       45

TGG  ATG  GGC  TGG  ATA  AAC  ACC  AAC  ACT  GGA  GAG  CCA  ACA  TAT  GCT  GAA     192
Trp  Met  Gly  Trp  Ile  Asn  Thr  Asn  Thr  Gly  Glu  Pro  Thr  Tyr  Ala  Glu
          50                        55                       60

GAG  TTC  AAG  GGA  CGG  TTT  GCC  TTC  TCT  TTG  GAA  ACC  TCT  GCC  AGC  ACT     240
Glu  Phe  Lys  Gly  Arg  Phe  Ala  Phe  Ser  Leu  Glu  Thr  Ser  Ala  Ser  Thr
 65                       70                        75                      80

GCC  TAT  TTG  CAG  ATC  AAC  AAC  CTC  AAA  AAT  GAG  GAC  ACG  GCT  ACA  TAT     288
Ala  Tyr  Leu  Gln  Ile  Asn  Asn  Leu  Lys  Asn  Glu  Asp  Thr  Ala  Thr  Tyr
               85                        90                       95

TTC  TGT  GGA  AGG  CAA  TTT  ATT  ACC  TAC  GGC  GGG  TTT  GCT  AAC  TGG  GGC     336
Phe  Cys  Gly  Arg  Gln  Phe  Ile  Thr  Tyr  Gly  Gly  Phe  Ala  Asn  Trp  Gly
          100                       105                      110

CAA  GGG  ACT  CTG  GTC  ACT  GTC  TCT  GCA  TCG  AGC  TCC  TCC  GGA  TCT  TCA     384
Gln  Gly  Thr  Leu  Val  Thr  Val  Ser  Ala  Ser  Ser  Ser  Ser  Gly  Ser  Ser
          115                       120                      125

TCT  AGC  GGT  TCC  AGC  TCG  AGC  GAT  ATC  GTC  ATG  ACC  CAG  TCT  CCT  AAA     432
Ser  Ser  Gly  Ser  Ser  Ser  Ser  Asp  Ile  Val  Met  Thr  Gln  Ser  Pro  Lys
          130                       135                      140

TTC  ATG  TCC  ACG  TCA  GTG  GGA  GAC  AGG  GTC  AGC  ATC  TCC  TGC  AAG  GCC     480
Phe  Met  Ser  Thr  Ser  Val  Gly  Asp  Arg  Val  Ser  Ile  Ser  Cys  Lys  Ala
145                       150                       155                     160

AGT  CAG  GAT  GTG  AGT  ACT  GCT  GTA  GCC  TGG  TAT  CAA  CAA  AAA  CCA  GGG     528
Ser  Gln  Asp  Val  Ser  Thr  Ala  Val  Ala  Trp  Tyr  Gln  Gln  Lys  Pro  Gly
               165                       170                      175

CAA  TCT  CCT  AAA  CTA  CTG  ATT  TAC  TGG  ACA  TCC  ACC  CGG  CAC  ACT  GGA     576
Gln  Ser  Pro  Lys  Leu  Leu  Ile  Tyr  Trp  Thr  Ser  Thr  Arg  His  Thr  Gly
               180                       185                      190

GTC  CCT  GAT  CCG  TTC  ACA  GGC  AGT  GGA  TCT  GGG  ACA  GAT  TAT  ACT  CTC     624
Val  Pro  Asp  Pro  Phe  Thr  Gly  Ser  Gly  Ser  Gly  Thr  Asp  Tyr  Thr  Leu
          195                       200                      205

ACC  ATC  AGC  AGT  GTG  CAG  GCT  GAA  GAC  CTG  GCA  CTT  CAT  TAC  TGT  CAG     672
Thr  Ile  Ser  Ser  Val  Gln  Ala  Glu  Asp  Leu  Ala  Leu  His  Tyr  Cys  Gln
     210                       215                      220

CAA  CAT  TAT  AGA  GTG  GCC  TAC  ACG  TTC  GGA  AGG  GGG  ACC  AAG  CTG  GAG     720
Gln  His  Tyr  Arg  Val  Ala  Tyr  Thr  Phe  Gly  Arg  Gly  Thr  Lys  Leu  Glu
```

```
                          225                               230                                235                                 240
ATA   AAA   CGG   GCT   GAT   GCT   GCA   CCA   ACT   GTA   TCC   ATC   TTC   CCA   CCA   TCC         768
Ile   Lys   Arg   Ala   Asp   Ala   Ala   Pro   Thr   Val   Ser   Ile   Phe   Pro   Pro   Ser
                        245                               250                                255

AGT   GAG   CAG   TTT   GAG   GGC   GGC   AGC   CTG   GCC   GCG   CTG   AAC   GCG   CAC   CAG         816
Ser   Glu   Gln   Phe   Glu   Gly   Gly   Ser   Leu   Ala   Ala   Leu   Asn   Ala   His   Gln
                  260                           265                                270

GCT   TGC   CAC   CTG   CCG   CTG   GAG   ACT   TTC   ACC   CGT   CAT   CGC   CAG   CCG   CGC         864
Ala   Cys   His   Leu   Pro   Leu   Glu   Thr   Phe   Thr   Arg   His   Arg   Gln   Pro   Arg
            275                           280                                285

GGC   TGG   GAA   CAA   CTG   GAG   CAG   TGC   GGC   TAT   CCG   GTG   CAG   CGG   CTG   GTC         912
Gly   Trp   Glu   Gln   Leu   Glu   Gln   Cys   Gly   Tyr   Pro   Val   Gln   Arg   Leu   Val
      290                                 295                         300

GCC   CTC   TAC   CTG   GCG   GCG   CGG   CTG   TCG   TGG   AAC   CAG   GTC   GAC   CAG   GTG         960
Ala   Leu   Tyr   Leu   Ala   Ala   Arg   Leu   Ser   Trp   Asn   Gln   Val   Asp   Gln   Val
305                           310                           315                                 320

ATC   CGC   AAC   GCC   CTG   GCC   AGC   CCC   GGC   AGC   GGC   GGC   GAC   CTG   GGC   GAA        1008
Ile   Arg   Asn   Ala   Leu   Ala   Ser   Pro   Gly   Ser   Gly   Gly   Asp   Leu   Gly   Glu
                              325                           330                                 335

GCG   ATC   CGC   GAG   CAG   CCG   GAG   CAG   GCC   CGT   CTG   GCC   CTG   ACC   CTG   GCC        1056
Ala   Ile   Arg   Glu   Gln   Pro   Glu   Gln   Ala   Arg   Leu   Ala   Leu   Thr   Leu   Ala
                  340                                 345                         350

GCC   GCC   GAG   AGC   GAG   CGC   TTC   GTC   CGG   CAG   GGC   ACC   GGC   AAC   GAC   GAG        1104
Ala   Ala   Glu   Ser   Glu   Arg   Phe   Val   Arg   Gln   Gly   Thr   Gly   Asn   Asp   Glu
            355                                 360                           365

GCC   GGC   GCG   GCC   AAC   GCC   GAC   GTG   GTG   AGC   CTG   ACC   TGC   CCG   GTC   GCC        1152
Ala   Gly   Ala   Ala   Asn   Ala   Asp   Val   Val   Ser   Leu   Thr   Cys   Pro   Val   Ala
370                           375                           380

GCC   GGT   GAA   TGC   GCG   GGC   CCG   GCG   GAC   AGC   GGC   GAC   GCC   CTG   CTG   GAG        1200
Ala   Gly   Glu   Cys   Ala   Gly   Pro   Ala   Asp   Ser   Gly   Asp   Ala   Leu   Leu   Glu
385                           390                           395                                 400

CGC   AAC   TAT   CCC   ACT   GGC   GCG   GAG   TTC   CTC   GGC   GAC   GGC   GGC   GAC   GTC        1248
Arg   Asn   Tyr   Pro   Thr   Gly   Ala   Glu   Phe   Leu   Gly   Asp   Gly   Gly   Asp   Val
                        405                           410                                 415

AGC   TTC   AGC   AAC   CGC   GGC   ACG   CAG   AAC   TGG   ACG   GTG   GAG   CGG   CTG   CTC        1296
Ser   Phe   Ser   Asn   Arg   Gly   Thr   Gln   Asn   Trp   Thr   Val   Glu   Arg   Leu   Leu
                  420                           425                                 430

CAG   GCG   CAC   CGC   CAA   CTG   GAG   GAG   CGC   GGC   TAT   GTG   TTC   GTC   GGC   TAC        1344
Gln   Ala   His   Arg   Gln   Leu   Glu   Glu   Arg   Gly   Tyr   Val   Phe   Val   Gly   Tyr
            435                           440                                 445

CAC   GGC   ACC   TTC   CTC   GAA   GCG   GCG   CAA   AGC   ATC   GTC   TTC   GGC   GGG   GTG        1392
His   Gly   Thr   Phe   Leu   Glu   Ala   Ala   Gln   Ser   Ile   Val   Phe   Gly   Gly   Val
      450                           455                           460

CGC   GCG   CGC   AGC   CAG   GAC   CTC   GAC   GCG   ATC   TGG   CGC   GGT   TTC   TAT   ATC        1440
Arg   Ala   Arg   Ser   Gln   Asp   Leu   Asp   Ala   Ile   Trp   Arg   Gly   Phe   Tyr   Ile
465                           470                           475                                 480

GCC   GGC   GAT   CCG   GCG   CTG   GCC   TAC   GGC   TAC   GCC   CAG   GAC   CAG   GAA   CCC        1488
Ala   Gly   Asp   Pro   Ala   Leu   Ala   Tyr   Gly   Tyr   Ala   Gln   Asp   Gln   Glu   Pro
                        485                           490                                 495

GAC   GCA   CGC   GGC   CGG   ATC   CGC   AAC   GGT   GCC   CTG   CTG   CGG   GTC   TAT   GTG        1536
Asp   Ala   Arg   Gly   Arg   Ile   Arg   Asn   Gly   Ala   Leu   Leu   Arg   Val   Tyr   Val
                  500                           505                                 510

CCG   CGC   TCG   AGC   CTG   CCG   GGC   TTC   TAC   CGC   ACC   AGC   CTG   ACC   CTG   GCC        1584
Pro   Arg   Ser   Ser   Leu   Pro   Gly   Phe   Tyr   Arg   Thr   Ser   Leu   Thr   Leu   Ala
            515                           520                                 525

GCG   CCG   GAG   GCG   GCG   GGC   GAG   GTC   GAA   CGG   CTG   ATC   GGC   CAT   CCG   CTG        1632
Ala   Pro   Glu   Ala   Ala   Gly   Glu   Val   Glu   Arg   Leu   Ile   Gly   His   Pro   Leu
      530                           535                                 540

CCG   CTG   CGC   CTG   GAC   GCC   ATC   ACC   GGC   CCC   GAG   GAG   GAA   GGC   GGG   CGC        1680
Pro   Leu   Arg   Leu   Asp   Ala   Ile   Thr   Gly   Pro   Glu   Glu   Glu   Gly   Gly   Arg
```

```
                545                       550                      555                      560
CTG   GAG   ACC   ATT   CTC   GGC   TGG   CCG   CTG   GCC   GAG   CGC   ACC   GTG   GTG   ATT        1728
Leu   Glu   Thr   Ile   Leu   Gly   Trp   Pro   Leu   Ala   Glu   Arg   Thr   Val   Val   Ile
                        565                     570                           575

CCC   TCG   GCG   ATC   CCC   ACC   GAC   CCG   CGC   AAC   GTC   GGC   GGC   GAC   CTC   GAC        1776
Pro   Ser   Ala   Ile   Pro   Thr   Asp   Pro   Arg   Asn   Val   Gly   Gly   Asp   Leu   Asp
                  580                           585                           590

CCG   TCC   AGC   ATC   CCC   GAC   AAG   GAA   CAG   GCG   ATC   AGC   GCC   CTG   CCG   GAC        1824
Pro   Ser   Ser   Ile   Pro   Asp   Lys   Glu   Gln   Ala   Ile   Ser   Ala   Leu   Pro   Asp
            595                           600                     605

TAC   GCC   AGC   CAG   CCC   GGC   AAA   CCG   CCG   CGC   GAG   GAC   CTG   AAG   TAA              1869
Tyr   Ala   Ser   Gln   Pro   Gly   Lys   Pro   Pro   Arg   Glu   Asp   Leu   Lys
      610                           615                           620
```

( 2 ) INFORMATION FOR SEQ ID NO:16:

( i ) SEQUENCE CHARACTERISTICS:
        ( A ) LENGTH: 622 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Asp   Pro   Glu   Ile   Gln   Leu   Val   Gln   Ser   Gly   Pro   Glu   Leu   Lys   Lys   Pro
1                       5                       10                            15

Gly   Glu   Thr   Val   Lys   Ile   Ser   Cys   Lys   Ala   Ser   Gly   Tyr   Thr   Phe   Thr
                  20                      25                            30

Asn   Tyr   Gly   Met   Asn   Trp   Val   Lys   Gln   Ala   Pro   Gly   Lys   Gly   Leu   Lys
            35                      40                            45

Trp   Met   Gly   Trp   Ile   Asn   Thr   Asn   Thr   Gly   Glu   Pro   Thr   Tyr   Ala   Glu
      50                            55                            60

Glu   Phe   Lys   Gly   Arg   Phe   Ala   Phe   Ser   Leu   Glu   Thr   Ser   Ala   Ser   Thr
65                            70                      75                            80

Ala   Tyr   Leu   Gln   Ile   Asn   Asn   Leu   Lys   Asn   Glu   Asp   Thr   Ala   Thr   Tyr
                        85                            90                            95

Phe   Cys   Gly   Arg   Gln   Phe   Ile   Thr   Tyr   Gly   Gly   Phe   Ala   Asn   Trp   Gly
                  100                           105                           110

Gln   Gly   Thr   Leu   Val   Thr   Val   Ser   Ala   Ser   Ser   Ser   Gly   Ser   Ser
                  115                           120                           125

Ser   Ser   Gly   Ser   Ser   Ser   Asp   Ile   Val   Met   Thr   Gln   Ser   Pro   Lys
            130                           135                     140

Phe   Met   Ser   Thr   Ser   Val   Gly   Asp   Arg   Val   Ser   Ile   Ser   Cys   Lys   Ala
145                           150                     155                           160

Ser   Gln   Asp   Val   Ser   Thr   Ala   Val   Ala   Trp   Tyr   Gln   Gln   Lys   Pro   Gly
                        165                           170                           175

Gln   Ser   Pro   Lys   Leu   Leu   Ile   Tyr   Trp   Thr   Ser   Thr   Arg   His   Thr   Gly
                  180                           185                     190

Val   Pro   Asp   Pro   Phe   Thr   Gly   Ser   Gly   Ser   Gly   Thr   Asp   Tyr   Thr   Leu
            195                           200                     205

Thr   Ile   Ser   Ser   Val   Gln   Ala   Glu   Asp   Leu   Ala   Leu   His   Tyr   Cys   Gln
      210                           215                     220

Gln   His   Tyr   Arg   Val   Ala   Tyr   Thr   Phe   Gly   Arg   Gly   Thr   Lys   Leu   Glu
225                           230                           235                           240

Ile   Lys   Arg   Ala   Asp   Ala   Ala   Pro   Thr   Val   Ser   Ile   Phe   Pro   Pro   Ser
                        245                     250                           255

Ser   Glu   Gln   Phe   Glu   Gly   Gly   Ser   Leu   Ala   Ala   Leu   Asn   Ala   His   Gln
                  260                           265                           270
```

```
Ala  Cys  His  Leu  Pro  Leu  Glu  Thr  Phe  Thr  Arg  His  Arg  Gln  Pro  Arg
          275                      280                     285

Gly  Trp  Glu  Gln  Leu  Glu  Gln  Cys  Gly  Tyr  Pro  Val  Gln  Arg  Leu  Val
     290                      295                     300

Ala  Leu  Tyr  Leu  Ala  Ala  Arg  Leu  Ser  Trp  Asn  Gln  Val  Asp  Gln  Val
305                      310                     315                          320

Ile  Arg  Asn  Ala  Leu  Ala  Ser  Pro  Gly  Ser  Gly  Gly  Asp  Leu  Gly  Glu
               325                     330                          335

Ala  Ile  Arg  Glu  Gln  Pro  Glu  Gln  Ala  Arg  Leu  Ala  Leu  Thr  Leu  Ala
          340                      345                          350

Ala  Ala  Glu  Ser  Glu  Arg  Phe  Val  Arg  Gln  Gly  Thr  Gly  Asn  Asp  Glu
          355                      360                          365

Ala  Gly  Ala  Ala  Asn  Ala  Asp  Val  Val  Ser  Leu  Thr  Cys  Pro  Val  Ala
     370                      375                          380

Ala  Gly  Glu  Cys  Ala  Gly  Pro  Ala  Asp  Ser  Gly  Asp  Ala  Leu  Leu  Glu
385                      390                     395                          400

Arg  Asn  Tyr  Pro  Thr  Gly  Ala  Glu  Phe  Leu  Gly  Asp  Gly  Gly  Asp  Val
               405                     410                          415

Ser  Phe  Ser  Asn  Arg  Gly  Thr  Gln  Asn  Trp  Thr  Val  Glu  Arg  Leu  Leu
               420                     425                          430

Gln  Ala  His  Arg  Gln  Leu  Glu  Glu  Arg  Gly  Tyr  Val  Phe  Val  Gly  Tyr
          435                      440                          445

His  Gly  Thr  Phe  Leu  Glu  Ala  Ala  Gln  Ser  Ile  Val  Phe  Gly  Gly  Val
     450                      455                          460

Arg  Ala  Arg  Ser  Gln  Asp  Leu  Asp  Ala  Ile  Trp  Arg  Gly  Phe  Tyr  Ile
465                      470                     475                          480

Ala  Gly  Asp  Pro  Ala  Leu  Ala  Tyr  Gly  Tyr  Ala  Gln  Asp  Gln  Glu  Pro
               485                     490                          495

Asp  Ala  Arg  Gly  Arg  Ile  Arg  Asn  Gly  Ala  Leu  Leu  Arg  Val  Tyr  Val
               500                     505                          510

Pro  Arg  Ser  Ser  Leu  Pro  Gly  Phe  Tyr  Arg  Thr  Ser  Leu  Thr  Leu  Ala
          515                      520                          525

Ala  Pro  Glu  Ala  Ala  Gly  Glu  Val  Glu  Arg  Leu  Ile  Gly  His  Pro  Leu
     530                      535                          540

Pro  Leu  Arg  Leu  Asp  Ala  Ile  Thr  Gly  Pro  Glu  Glu  Glu  Gly  Gly  Arg
545                      550                     555                          560

Leu  Glu  Thr  Ile  Leu  Gly  Trp  Pro  Leu  Ala  Glu  Arg  Thr  Val  Val  Ile
               565                     570                          575

Pro  Ser  Ala  Ile  Pro  Thr  Asp  Pro  Arg  Asn  Val  Gly  Gly  Asp  Leu  Asp
               580                     585                          590

Pro  Ser  Ser  Ile  Pro  Asp  Lys  Glu  Gln  Ala  Ile  Ser  Ala  Leu  Pro  Asp
          595                      600                          605

Tyr  Ala  Ser  Gln  Pro  Gly  Lys  Pro  Pro  Arg  Glu  Asp  Leu  Lys
     610                      615                     620
```